US010878950B1

(12) United States Patent
Jun et al.

(10) Patent No.: US 10,878,950 B1
(45) Date of Patent: Dec. 29, 2020

(54) VERIFYING DATA ACCURACY IN PRIVACY-PRESERVING COMPUTATIONS

(71) Applicant: Healthblock, Inc., Palo Alto, CA (US)

(72) Inventors: Brian Jun, Mountain View, CA (US); Jan T. Liphardt, Palo Alto, CA (US)

( * ) Notice: Subject to any disclaimer, the term of this patent is extended or adjusted under 35 U.S.C. 154(b) by 0 days.

(21) Appl. No.: 16/537,523

(22) Filed: Aug. 9, 2019

(51) Int. Cl.
*G16H 10/60* (2018.01)
*G06Q 40/08* (2012.01)

(52) U.S. Cl.
CPC ............ *G16H 10/60* (2018.01); *G06Q 40/08* (2013.01)

(58) Field of Classification Search
CPC ... G16H 10/60; G06Q 40/08; G06Q 50/22–24
See application file for complete search history.

(56) References Cited

U.S. PATENT DOCUMENTS

| 7,197,642 | B2 * | 3/2007 | Walmsley | H04L 9/3271 380/259 |
|---|---|---|---|---|
| 2005/0091101 | A1 | 4/2005 | Epling et al. | |
| 2009/0094065 | A1 * | 4/2009 | Hyde | G06F 19/328 705/4 |
| 2015/0227697 | A1 | 8/2015 | Nelson et al. | |
| 2016/0328621 | A1 | 11/2016 | Negi et al. | |
| 2018/0101697 | A1 | 4/2018 | Rene et al. | |
| 2018/0234234 | A1 | 8/2018 | Hurley et al. | |
| 2019/0156426 | A1 * | 5/2019 | Drucker | G06Q 40/08 |
| 2019/0229907 | A1 | 9/2019 | Nicolson et al. | |
| 2019/0311813 | A1 * | 10/2019 | Hie | G16H 80/00 |

OTHER PUBLICATIONS

Cunningham R., Fuller B., Yakoubov S. (2017) Catching MPC Cheaters: Identification and Openability. In: Shikata J. (eds) Information Theoretic Security. ICITS 2017. Lecture Notes in Computer Science, vol. 10681. pp. 106 and 112. Springer, Cham. https://doi.org/10.1007/978-3-319-72089-0_7 (Year: 2017).*
"Actively Secure Two-party Computation", Pullonen, Pille, dated May 20, 2013, 101 pages.
"Efficient Multiparty Protocols Using Circuit Randomization", Beaver, Donald, dated Aug. 11, 1991, 13 pages.

* cited by examiner

*Primary Examiner* — Robert A Sorey
(74) *Attorney, Agent, or Firm* — Patrick E. Caldwell, Esq.; The Caldwell Firm, LLC

(57) ABSTRACT

Methods, systems and computer program products for data analytics. An information ecosystem comprises a plurality of participants and a plurality of data sets associated with the participants. An event initiates performance of a computation over different obfuscated data sets to determine an obfuscated computational result. An integrity value pertaining to constituent data of the different obfuscated data sets and, correspondingly, an integrity value pertaining to the computational result itself, is quantified by checking if the earlier offered data set or any constituents thereof are consistent with one or more aspects of later retrieved data. Certain variations of methods, systems and computer program products are used for verifying data accuracy in privacy-preserving computations that are performed in a health ecosystem where the data sets pertain to health information associated with the participants. When the integrity value is below a threshold, the data is deemed to include falsified or inaccurate data.

30 Claims, 11 Drawing Sheets

VERIFYING DATA ACCURACY IN PRIVACY-PRESERVING COMPUTATIONS

FIELD

This disclosure relates to data analytics, and more particularly to techniques for verifying data accuracy in privacy-preserving computations.

BACKGROUND

Modern computing environments facilitate the sharing of many types of data from multiple participants. This data is shared among the participants for a variety of purposes. For example, data that constitute text messages, photographs, videos, files, or other content objects might be shared (e.g., via email, text messages, etc.) between the participants. In performing such sharing, the data shared is often presented by a first participant (e.g., data owner) to a second participant (e.g., data recipient) without any attempt to obfuscate the data.

In other cases, however, two or more participants may be motivated to exchange data, but none of the two or more participants are willing to disclose unobfuscated data to the other participants. Consider the case of a medical insurance applicant and a medical insurance company that desire to exchange certain data to compute a risk score for determining the insurability of the applicant and/or for determining the applicant's premium costs. In this case, the applicant may want to protect, or preserve the privacy or ownership of, certain personal health information (e.g., the applicant's genome sequence). At the same time, the insurance company may want to protect, or preserve the privacy or ownership of, its own proprietary risk model (e.g., comprising actuarial tables, risk weightings, etc.). Still, the health information needs to be applied to the risk model to achieve the mutually desired outcome—a determination of insurability and calculation of insurance premium costs.

It is axiomatic that when performing such privacy-preserving data computations or analytics, the accountability of the participants to provide accurate and complete data is critical. In the foregoing case, the insurance company is expecting the applicant to be accountable for providing complete and truthful health information. Likewise, the applicant expects the insurance company to not tamper with the applicant's inputs and furthermore, the applicant expects the insurance company to consistently apply its risk model when evaluating the insurability of the applicant.

Unfortunately, privacy-preserving computation techniques are deficient in situations that include respective sets of data from two or more participants that are not only to be protected while performing computations, but also are to be usable for substantiating participant accountability. When many participants are involved, such as with crowd-sourced data sets, the subject data can be obfuscated using certain known techniques (e.g., differential privacy techniques). For example, a pharmaceutical company can analyze a set of genome information from a large population of participants to determine certain associations between genetic variations and traits or conditions on a population level without needing to see the raw genome data of the individual participants. However, such techniques are not applicable to situations involving, for example, just two participants (e.g., a patient and their doctor), where the data from either party (e.g., genome sequence, risk model parameters, etc.) cannot be obfuscated by mixing the data into a larger set of data and/or cannot be otherwise anonymized.

Data protection or privacy preservation during computations is further complicated when the two or more participants (e.g., an insurance applicant and an insurance company or a patient and their doctor) each have data that is to be protected. Moreover, the fact that the underlying data is protected when performing privacy-preserving computations presents challenges in situations where the underlying data is to be verifiably complete and accurate. Specifically, many known privacy-preserving computation techniques offer no recourse for verifying the underlying data when the accountability of one or more respective participants is questioned. What is needed is a way to achieve meaningful analytical or computational results from the data of two or more participants while preserving the privacy of the data—and yet without trading off the verifiability of the data.

SUMMARY

The present disclosure describes techniques used in systems, methods, and in computer program products for verifying data accuracy in privacy-preserving computations, which techniques advance the relevant technologies to address technological issues with legacy approaches. Certain embodiments are directed to technological solutions for implementing a framework for performing computations over sets of data from two or more participants while preserving data privacy and participant accountability.

The disclosed embodiments modify and improve over legacy approaches. In particular, the herein-disclosed techniques provide practical applications of technical solutions that address the technical problems attendant to performing privacy-preserving computations without trading off the verifiability of the underlying data or the computation results themselves. Such technical solutions involve specific implementations (i.e., data organization, data communication paths, module-to-module interrelationships, etc.) that relate to the software arts for improving computer functionality when performing privacy-preserving computations.

Many of the herein-disclosed techniques operate within a computer-to-computer communication framework that implements a protocol for performing computations over sets of data from two or more participants while preserving data privacy and participant accountability. The techniques for preserving data privacy without trading off participant accountability overcome long-standing yet heretofore unsolved technological problems associated with the lack of transparency and accountability when computer systems are tasked with performing privacy-preserving computations.

Further details of aspects, objectives, and advantages of the technological embodiments are described herein, and in the drawings and claims.

BRIEF DESCRIPTION OF THE DRAWINGS

The drawings described below are for illustration purposes only. The drawings are not intended to limit the scope of the present disclosure.

DETAILED DESCRIPTION

Figure 1:
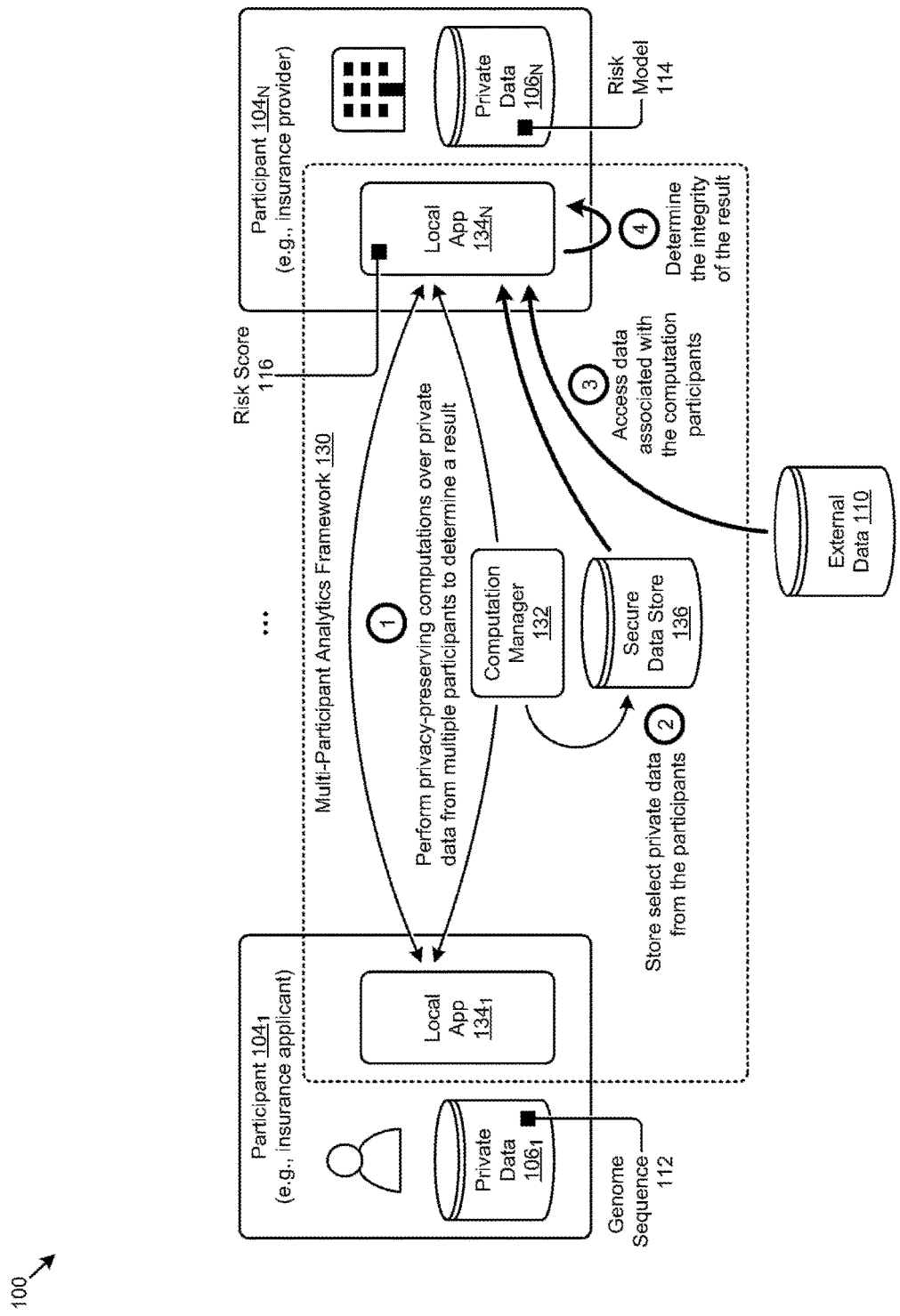
FIG. 1 illustrates a computing environment in which embodiments of the present disclosure can be implemented.

Aspects of the present disclosure solve problems associated with a lack of transparency and verifiability of data used in privacy-preserving computations. These problems are unique to, and may have been created by, various computer-implemented methods for implementing privacy-preserving computations. Some embodiments are directed to approaches for implementing a framework for performing computations over sets of data from two or more participants while preserving data privacy and participant accountability. The accompanying figures and discussions herein present example environments, systems, methods, and computer program products for verifying data accuracy in privacy-preserving computations.

Overview

Disclosed herein are techniques for implementing a framework for performing computations over sets of data from two or more participants while preserving data privacy and participant accountability. In certain embodiments, the framework is implemented in an information ecosystem having a plurality of participants that desire to perform privacy-preserving computations over data sets from the participants. As an example, the information ecosystem might be a health ecosystem comprising at least two participants: an insurance applicant and an insurance company. In this case, both participants have respective data sets (e.g., genome sequence data and risk model data, respectively) that the participants want to keep private, but also want to combine so as to determine a risk score for underwriting and pricing of an insurance policy.

Certain techniques facilitated by the framework are applied to the data sets from the participants to determine one or more computation results while preserving the privacy of the data sets. If a data integrity check event is detected, certain verification operations facilitated by the framework are performed to determine various attributes (e.g., accuracy, completeness, etc.) of any of the data sets or the computation results. For example, a data integrity check event might be invoked to check the accuracy of the input (e.g., questionnaire responses) provided by an insurance applicant if a computed risk score is below a specified threshold value (e.g., the risk score is particularly low). In certain embodiments, various portions of the private data used to determine the computation results are accessed to facilitate the verification operations and/or determine the data attributes. In certain embodiments, various external data are accessed to facilitate the verification operations and/or determine the data attributes. In certain embodiments, a data attribute might be a data accuracy probability. In certain embodiments, one or more sets of executable code are installed at the computing devices of a respective one or more participants to carry out the operations facilitated by the framework.

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Descriptions of Example Embodiments

FIG. 1 illustrates a computing environment 100 in which embodiments of the present disclosure can be implemented. As an option, one or more variations of computing environment 100 or any aspect thereof may be implemented in the context of the architecture and functionality of the embodiments described herein.

FIG. 1 illustrates aspects pertaining to implementing a framework for performing computations over sets of data from two or more participants while preserving data privacy and participant accountability. Specifically, the figure presents a logical depiction of how the herein disclosed techniques can be implemented in a framework in a computing environment to verify the integrity of data sets and/or results associated with privacy-preserving computations over the data sets. A representative set of high order operations are also presented to illustrate how the herein disclosed techniques might be applied to privacy-preserving computations associated with an insurance applicant and an insurance provider in a health ecosystem.

As depicted in FIG. 1, computing environment 100 illustrates a set of representative participants (e.g., participant $104_1, \ldots,$ participant $104_N$) associated with an information ecosystem. For example, participant $104_1$ might be an insurance applicant and participant $104_N$ might be an insurance provider in a health ecosystem. The two representative participants in the ecosystem have a desire to perform certain computations over data owned by the participants while preserving the privacy or protection of the data. In the foregoing example, the insurance applicant and insurance provider might desire to exchange certain data to compute a risk score for determining the insurability of the applicant and/or premium costs. Specifically, a genome sequence 112 of participant $104_1$ might be applied to a risk model 114 of participant $104_N$ to determine the risk score. As can be observed, however, genome sequence 112 is data (e.g., private data $106_1$) that participant $104_1$ does not want to openly share with participant $104_N$, and risk model 114 is data (e.g., private data $106_N$) that participant $104_N$ does not want to openly share with participant $104_1$.

As can be observed in computing environment 100, the herein disclosed techniques can be implemented in a multi-participant analytics framework 130 to facilitate the desired computation (e.g., risk score calculation) between participant $104_1$ and participant $104_N$ while preserving the privacy of their respective data sets (e.g., genome sequence 112 and risk model 114). Specifically, an instance of an application (e.g., local app $134_1$, and local app $134_N$) delivered to and installed at each participant can cooperate with a computation manager 132 in multi-participant analytics framework 130 to perform privacy-preserving computations over the private data associated with the participants (operation 1). For example, the herein disclosed techniques can facilitate the application of genome sequence 112 to risk model 114 to compute a risk score 116 while preserving the privacy of genome sequence 112 and risk model 114.

Such privacy-preserving computations are achieved by a combination of data protection and obfuscation techniques such as oblivious transfers, random shares, Beaver triple arithmetic, and/or other techniques. Moreover, the herein disclosed techniques preserve the privacy of the data over all involved participants including the data owners, computation providers, and/or other involved participants. In the scenario shown, for example, privacy of genome sequence 112 and risk model 114 is preserved over participant $104_1$, participant $104_N$, and the one or more participants associated with computation manager 132. In some situations, an instance of an application or application agent (e.g., and agent of local app $134_1$ or an agent of local app $134_N$) can be delivered to, and installed onto, a storage facility that is accessible by computation manager 132.

As earlier mentioned, the accountability of the participants to provide accurate and complete data is critical. In the foregoing case, the insurance provider is expecting the insurance applicant to be accountable for providing complete and truthful health information. Likewise, the applicant expects the insurance company to not tamper with the applicant's inputs and to consistently apply its risk model when evaluating the insurability of applicants. The fact that the underlying data is protected when performing privacy-preserving computations presents challenges in situations where the underlying data is to be verifiably complete and accurate. Still, a participant may desire some recourse for verifying the underlying data when the accountability of one or more respective participants is questioned, such as when an insurance provider suspects that an insurance applicant had lied or wasn't forthcoming with his or her responses on an application.

The herein disclosed techniques address the foregoing problems attendant to a lack of transparency of the underlying data in privacy-preserving computations by facilitating various data integrity checks over the private data sets and/or computation results. If a data integrity check event is invoked, certain verification operations facilitated by the techniques disclosed herein are performed to determine an integrity value 315 and other various attributes (e.g., accuracy, completeness, etc.) of any of the data sets or the computation results. For example, a data integrity check event might be invoked by the insurance provider to check the accuracy of the input (e.g., questionnaire responses) provided by the insurance applicant if a computed risk score is below a specified threshold value (e.g., the risk score is particularly low). The foregoing are merely examples. As used herein, an integrity value is a numeric representation of a likelihood that an earlier offered data set is consistent with one or more aspects of later retrieved data. In some cases, an integrity value is a numeric representation of a likelihood that one or more aspects of the earlier offered data set was wrong, or a lie, or at least partially untruthful, or at least partially incomplete. In some cases, an integrity value is calculated by one or more integrity checks.

As shown, such data integrity checks can be facilitated at least in part by storing select portions of the participants' data sets that are used to perform the computations (operation 2). Such select private data may be stored in a secure data store 136 in multi-participant analytics framework 130. A participant performing a data integrity check can access the select data in secure data store 136 and/or other data associated with the participants and/or any results from the computations (operation 3). For example, various sets of external data 110 (e.g., public data, other obfuscated data, etc.) might be accessed to facilitate a data integrity check. In one exemplary embodiment of operation 3, one or more external corpora that comprise information that is not available in the secure data store is accessed for the purpose of facilitating a data integrity check. In another exemplary embodiment of operation 3, one or more external corpora are accessed to retrieve information that was not available at the time that the computations of operation 2 were performed. In another embodiment of operation 3, one or more external corpora are accessed to retrieve information that was not derived from the computations of operation 2.

The foregoing data and/or other information (e.g., rules, etc.) are analyzed to determine the integrity of the computation result and/or the underlying data sets (operation 4). As merely one example, a data accuracy probability might be determined as an objective measure of data integrity.

Application of the foregoing techniques and/or other techniques disclosed herein overcome long standing yet previously unsolved technological problems associated with a lack of transparency of the underlying data in privacy-preserving computations that arise in the realm of computer systems. Specifically, the herein disclosed techniques efficiently facilitate verification of the data sets and/or computation results of multi-party privacy-preserving computations even when the data sets are protected.

One embodiment of techniques for performing and verifying multi-participant privacy-preserving computations is disclosed in detail as follows.

Figure 2:
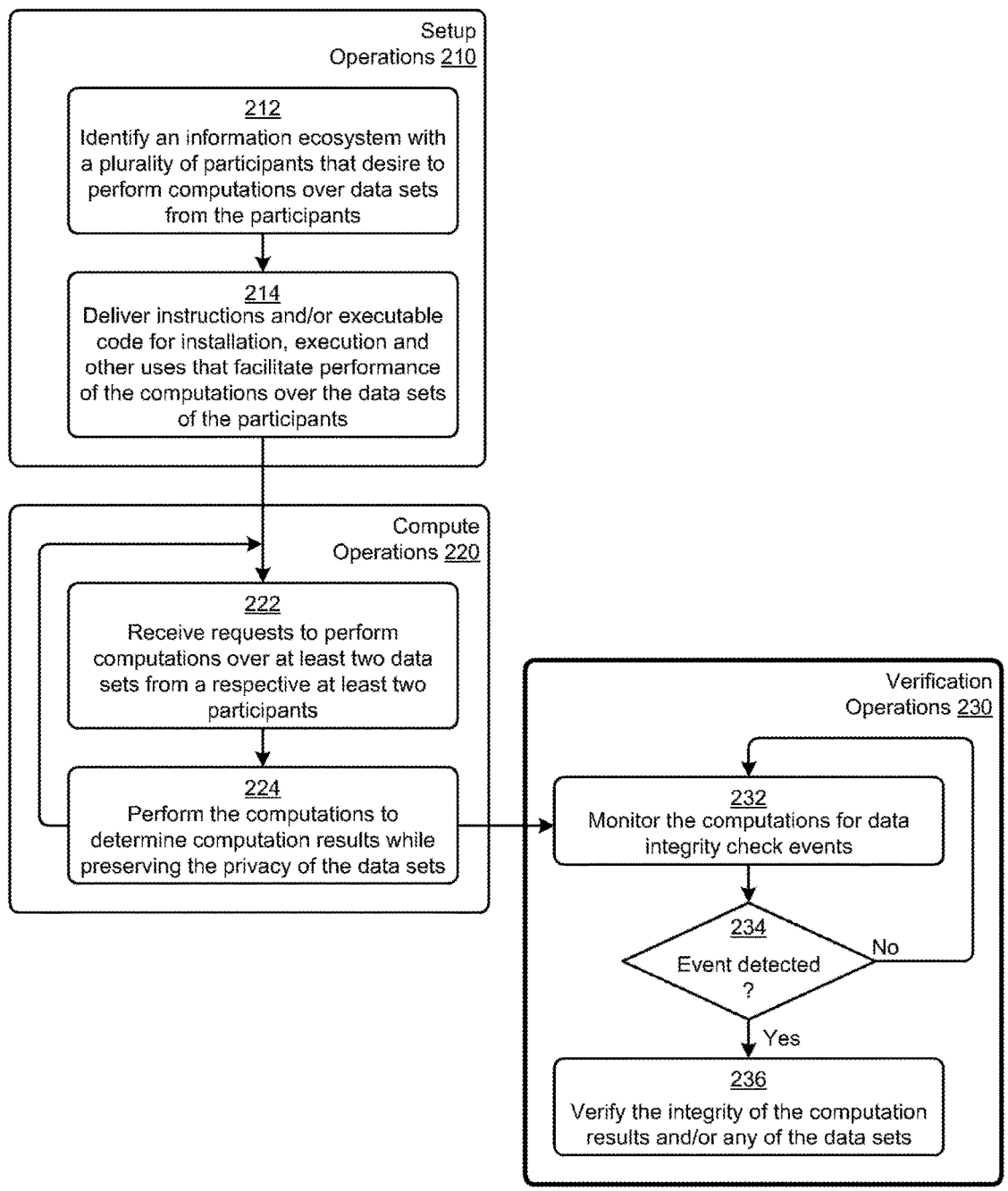
FIG. 2 depicts a multi-participant privacy-preserving computation technique as implemented in systems that verify accuracy of data used in privacy-preserving computations, according to an embodiment.

FIG. 2 depicts a multi-participant privacy-preserving computation technique 200 as implemented in systems that verify accuracy of data used in privacy-preserving computations. As an option, one or more variations of multi-participant privacy-preserving computation technique 200 or any aspect thereof may be implemented in the context of the architecture and functionality of the embodiments described herein. The multi-participant privacy-preserving computation technique 200 or any aspect thereof may be implemented in any environment.

FIG. 2 illustrates aspects pertaining to implementing a framework for performing computations over sets of data from two or more participants while preserving data privacy and participant accountability. Specifically, the figure is presented to illustrate one embodiment of certain steps and/or operations performed over various devices (e.g., user devices, servers, systems, etc.) to facilitate analytics and computations over data sets from multiple participants that both preserve the privacy of the data sets and allow for verification of data sets and/or computation results. As can be observed, the steps and/or operations can be grouped into a set of setup operations 210, a set of compute operations 220, and a set of verification operations 230.

The setup operations 210 of multi-participant privacy-preserving computation technique 200 commence by identifying an information ecosystem that comprises a plurality of participants that desire to perform computations over data sets from the participants (step 212). As an example, a health ecosystem might comprise patients, physicians, pharmacists, scientists, analysts and others associated with various entities (e.g., hospitals, pharmacies, pharmaceutical companies, etc.) that each have data sets they own and manage. These participants in the ecosystem may want to allow use of their data sets to achieve meaningful analytical and/or computational results, but not want to openly disclose the underlying data to the other participants.

To help facilitate such privacy-preserving computations, a set of instructions and/or executable code might be delivered for use by one or more of the participants in the ecosystem (step 214). In some cases, the instructions are codified into a set of executable code (e.g., an application) that instructs a processor of a computing device to carry out operations. In some cases, the instructions are in the form of an interpreted language (e.g., Python). In some cases, the instructions are in the form of commands to be delivered to a specialized browser and/or used to carry out a protocol with a server (e.g., a WebRTC signaling server). In some cases, the instructions comprise parameters (e.g., IP address information) that are used by a specialized browser and/or a specialized server that are configured to carry out full duplex (e.g., peer-to-peer) communications between a first peer computing device and an identified second peer computing device.

The compute operations 220 commence by receiving requests to perform computations over at least two data sets from respective participants in the information ecosystem (step 222). Such requests might be received by the executable code and/or other components that are implemented to facilitate the multi-participant privacy-preserving computation technique 200. In accordance with the requests, computations are performed over the data sets to determine one or more computation results while preserving the privacy of the data sets (step 224). Such privacy-preserving computations are achieved by various combinations of data protection and obfuscation techniques as facilitated by embodiments of the herein disclosed techniques. As illustrated in multi-participant privacy-preserving computation technique 200, compute operations 220 can be continuously performed in an information ecosystem.

As earlier described, verification of the data sets and/or the results of the privacy-preserving computations may be desired by one or more participants. The verification operations 230 of multi-participant privacy-preserving computation technique 200 facilitate such verifications by monitoring so as to detect data integrity check events (step 232). Such data integrity check events might be triggered before, upon, or after the determination of a computation result. In some cases, the data sets exchanged, or portions thereof, can be gathered and tracked for use in later data integrity check operations. If no data integrity event is detected ("No" path of decision 234), monitoring for data integrity check events continues.

When a data integrity event is detected ("Yes" path of decision 234), the integrity of the computation results and/or the underlying data sets associated with the computation results is verified (step 236). In many cases, one or more data attributes associated with a data set can serve as a quantitative measure of the integrity of the data. As merely one example, a measure of the probability that a particular data set is accurate might be determined to verify the integrity of the data set. In this case, if the probability is below a certain threshold, the data set may be deemed to include falsified data, or at least inaccurate data. In any case, verification operations 230 performed in accordance with the techniques herein disclosed facilitate the verification of the data sets and/or computation results associated with privacy-preserving computations.

One embodiment of a system, data flows, and data structures for implementing the multi-participant privacy-preserving computation technique 200 and/or other herein disclosed techniques is disclosed as follows.

Figure 3:
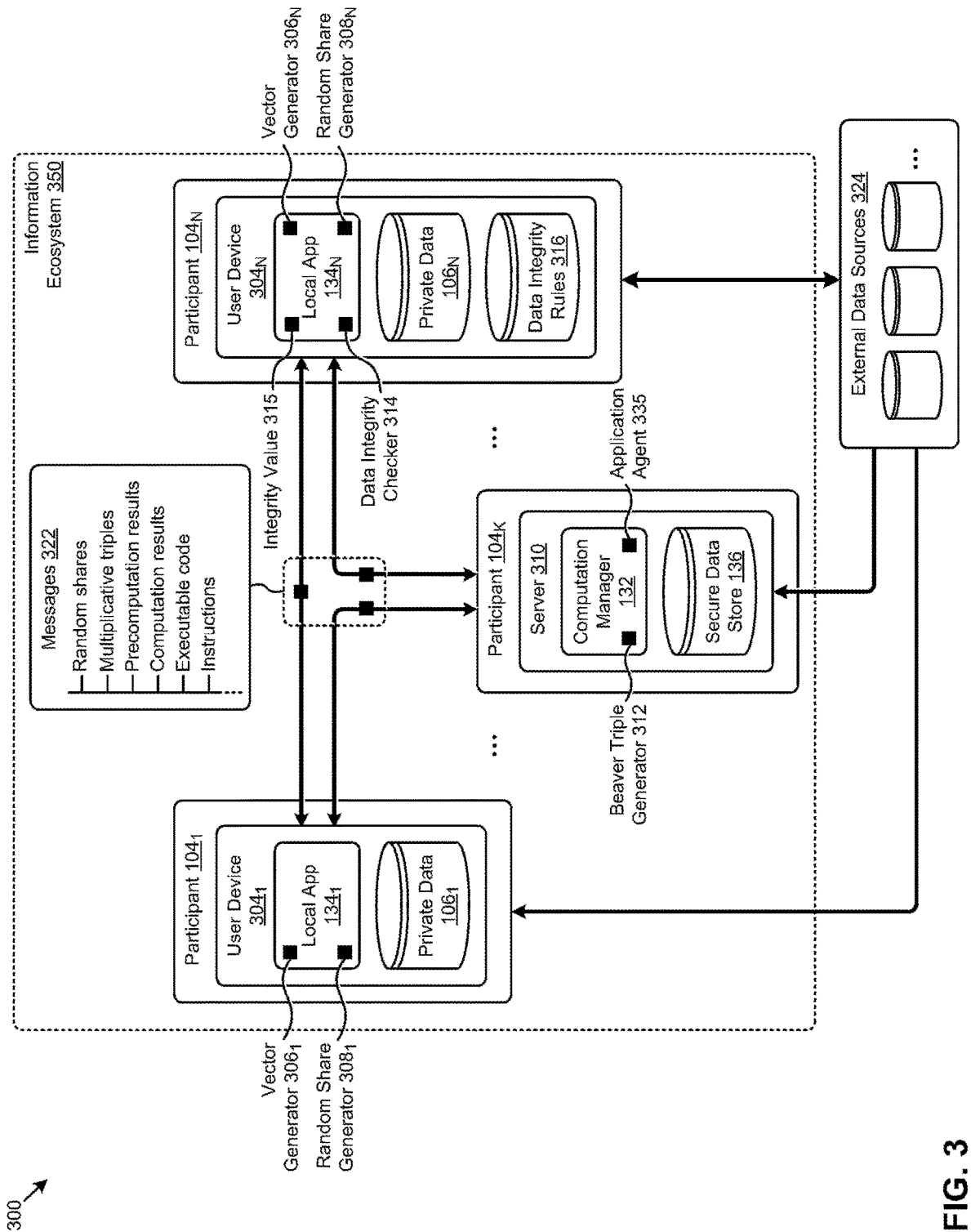
FIG. 3 presents a block diagram of a system that verifies data accuracy in privacy-preserving computations, according to an embodiment.

FIG. 3 presents a block diagram of a system 300 that verifies data accuracy in privacy-preserving computations. As an option, one or more variations of system 300 or any aspect thereof may be implemented in the context of the architecture and functionality of the embodiments described herein. The system 300 or any aspect thereof may be implemented in any environment.

FIG. 3 illustrates aspects pertaining to implementing a framework for performing computations over sets of data from two or more participants while preserving data privacy and participant accountability. Specifically, the figure is being presented to show one embodiment of certain representative components and associated data structures and data flows implemented in a computing environment to facilitate the herein disclosed techniques.

As can be observed, the aforementioned components, data flows, and data structures are associated with a set of participants in an information ecosystem 350 (e.g., health ecosystem). The participants of the ecosystem are represented by participant $104_1$, participant $104_K$, and participant $104_N$. As merely one example, participant $104_1$ and participant $104_N$ might desire to perform multi-participant privacy-preserving computations, whereas participant $104_K$ might be an entity (e.g., a data protection provider) in the ecosystem that facilitates the execution and verification of the multi-participant privacy-preserving computations.

In the shown embodiment, an instance of computation manager 132 earlier described is operating at a server 310 associated with participant $104_K$. Furthermore, instances of an application (e.g., local app $134_1$, . . . , local app $134_N$) are also installed on the user devices (e.g., user device $304_1$ . . . , user device $304_N$) of various respective participants (e.g., participant $104_1$ . . . , participant $104_N$) to facilitate the execution and verification of the multi-participant privacy-preserving computations. In some cases, sets of executable code that comprise the applications (e.g., apps) are delivered by a participant (e.g., participant $104_K$) in information ecosystem 350 for installation on various computing devices.

In some situations, the various computing devices includes storage devices such as is depicted by secure data store 136. The computing devices of the participants are capable of accessing various instances of external data sources 324 in order to, for example, facilitate verification of computation results and/or participant data.

As illustrated, the computing devices (e.g., user devices, servers, etc.) associated with the participants in the information ecosystem communicate with each other using instances of messages 322. Messages 322 carry various information (e.g., random shares, multiplicative triples, pre-computation results, computation results, executable code, etc.) that facilitates the execution and verification of privacy-preserving computations according to the herein disclosed techniques. Some of the aforementioned information carried by messages 322 is further described in the following.

As can be observed, various agents are implemented at the computing devices of the participants to facilitate the execution of privacy-preserving computations over the data sets (e.g., private data $106_1$, . . . , private data $106_N$) of the participants in information ecosystem 350. For example, instances of a vector generator (e.g., vector generator $306_1$, . . . , vector generator $306_N$) operating at each local app serve to prepare a data set for computation by vectorizing certain data from the participant's private data. Instances of a random share generator (e.g., random share generator $308_1$, . . . , random share generator $308_N$) at the local apps facilitate the sharing of portions (e.g., random shares) of a participant's data (e.g., vectors) with other participants while preserving the privacy of the data.

The local applications at the user devices are also capable of performing certain local computations (e.g., precomputations) over the local private data and any private data received from other participants. Such local computations might be facilitated at least in part by various information provided by computation manager 132. For example, a Beaver triple generator 312 operating at computation manager 132 on server 310 might provide Beaver triples from which multiplicative triple factors can be provided to the participants of a privacy-preserving computation to facilitate various computations at the participants.

In some cases, computation manager 132 receives pre-computation results from the participants that can be combined to determine one or more computation results. The computation results are then communicated to those participants authorized to receive them. Additionally, in some embodiments, computation manager 132 hosts an application agent 335 that communicates cooperatively with local app $134_1$, . . . , local app $134_N$. The application agent might 335 access and/or store profile data (e.g., participant profile data) to/from a secure storage area. The application agent 335 can be configured to access the secure storage area in a privacy-observant manner.

Various other agents are implemented at the computing devices of the participants to facilitate the verification of the computation results—and/or the data sets used to determine the results—in accordance with the herein disclosed techniques. As shown, an instance of secure data store 136 is implemented at server 310 to store select portions of the private data exchanged between the participants of a privacy-preserving computation. For example, computation manager 132 might intercept certain instances of message 322 that carry such private data in order to extract select portions of the private data for storage in secure data store 136.

As shown in this embodiment, a data integrity checker 314 within local app $134_N$ at user device $304_N$ of participant $104_N$ monitors any private data and/or computation results received at user device $304_N$ to determine if a data integrity check event is to be triggered. In some cases, data integrity checker 314 might access a set of data integrity rules 316 to determine whether a data integrity check event is to be triggered. If such an event is triggered, data integrity checker 314 can access certain information at secure data store 136, external data sources 324, and/or other sources to determine various attributes pertaining to the data set that is being verified. Such data attributes can then be analyzed to determine whether the data set is acceptable. As a specific example, data integrity checker 314 might analyze the foregoing information from the data sources to determine a probability that a particular data set is accurate. The probability level is then applied to the data integrity rules 316 by data integrity checker 314 to determine an acceptability of the data set.

The components, data flows, and data structures shown in FIG. 3 present merely one example partitioning and associated data manipulation approaches. The specific example shown is purely exemplary and other subsystems, data structures, and/or partitioning are reasonable. In one alternative embodiment, some or all of the functionality earlier described as associated with participant $104_K$ are provided by one or more secure enclaves associated with the computing devices of the participants in information ecosystem 350. As used herein, a secure enclave is a storage area of a computing device that has one or more access controls in addition to access controls that are provided by the file system of the computing device. Such additional access controls may be provided by operating system components that extend the functionality of the file system of the computing device.

The foregoing discussions include techniques for executing privacy-preserving computations between two or more participants (e.g., compute operations 220 of FIG. 2), which techniques and data are disclosed in further detail as follows.

Figure 4:
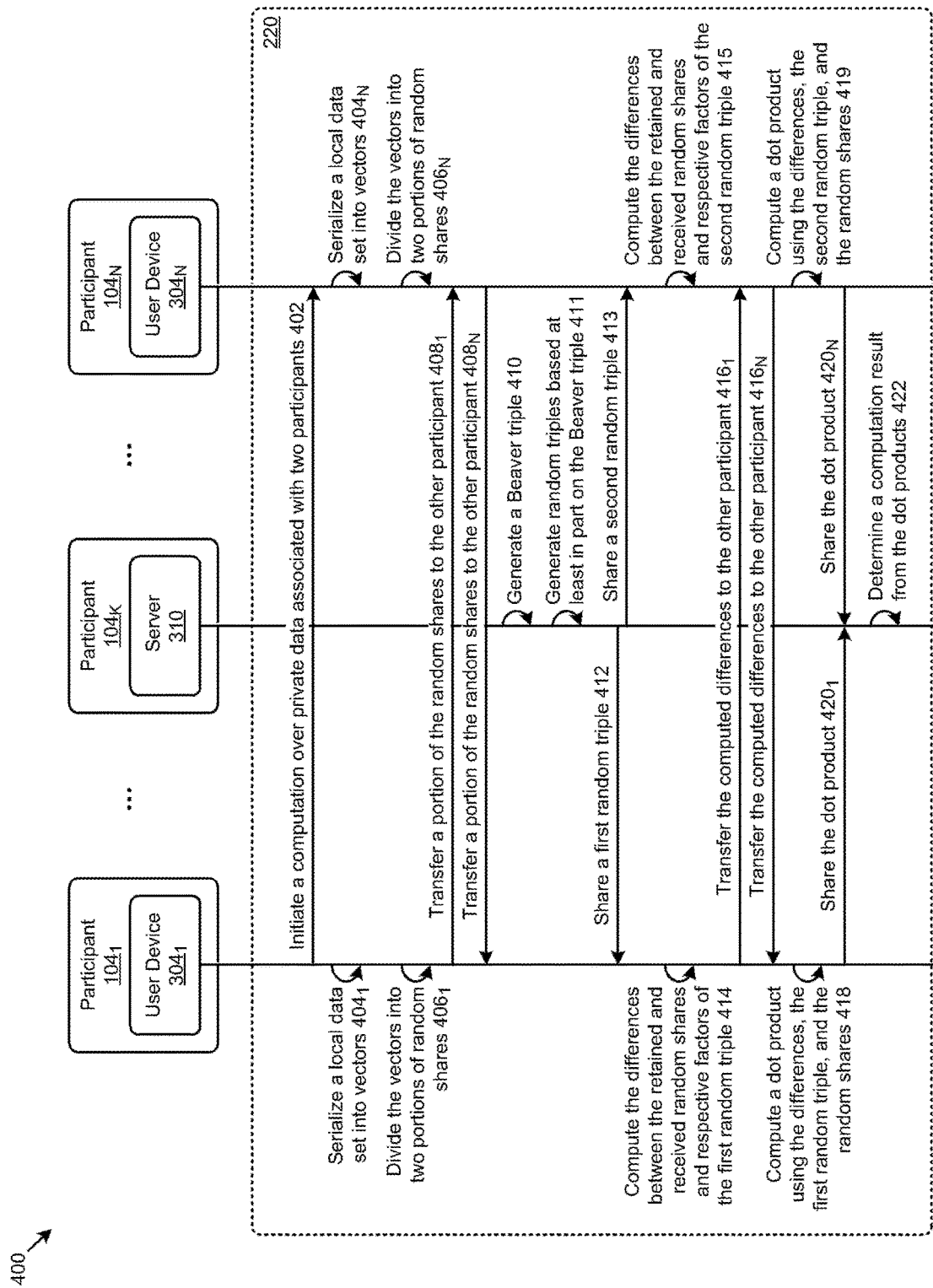
FIG. 4 depicts a privacy-preserving computation technique as implemented in systems that verify data accuracy in privacy-preserving computations, according to an embodiment.

FIG. 4 depicts a privacy-preserving computation technique 400 as implemented in systems that verify data accuracy in privacy-preserving computations. As an option, one or more variations of privacy-preserving computation technique 400 or any aspect thereof may be implemented in the context of the architecture and functionality of the embodiments described herein. The privacy-preserving computation technique 400 or any aspect thereof may be implemented in any environment.

FIG. 4 illustrates aspects pertaining to implementing a framework for performing computations over sets of data from two or more participants while preserving data privacy and participant accountability. Specifically, the figure is being presented to illustrate a representative two-participant privacy-preserving computation scenario as facilitated by the herein disclosed techniques for executing privacy-preserving computations between two or more participants (e.g., compute operations 220 of FIG. 2). More specifically, the privacy-preserving computation technique 400 is illustrated by a privacy-preserving computation scenario carried out by participant $104_1$ and participant $104_N$ with support from participant $104_K$. The high order interactions (e.g., operations, messages, etc.) over the participants involved in the scenario are performed by the various computing components earlier described. The particular computing components shown in FIG. 4 are user device $304_1$ and user device $304_N$ of participant $104_1$ and participant $104_N$, respectively, and server 310 of participant $104_K$.

Privacy-preserving computation technique 400 commences with participant $104_1$ initiating a computation over private data sets associated with participant $104_1$ and participant $104_N$ (message 402). As an example, the participants might have executable code (e.g., applications or apps) on their user devices that facilitate the initiation of such privacy-preserving computations. To prepare the data sets for the privacy-preserving computations, the data set local to each participant is serialized into vectors (operation $404_1$ and operation $404_N$). The serialization of the data sets facilitates, for example, certain operations and/or computations (e.g., additions, subtractions, multiplications, dot products, etc.) to be performed over the data sets from the participants. The resulting sets of vectors are each divided into two portions of random shares (operation $406_1$ and operation $406_N$). Random shares, as used herein, are randomized instances of a set of data inputs. The random shares serve to obfuscate the underlying data inputs to facilitate sharing of, and operations over, the data inputs while preserving their privacy.

A portion of the random shares of participant $104_1$ are transferred to participant $104_N$ (message $408_1$), and a portion of the random shares of participant $104_N$ are transferred to participant $104_1$ (message $408_N$). In some cases, the privacy of the underlying data sets of the participants is further protected by transferring the random shares in accordance with an oblivious transfer protocol. Oblivious transfer, as used herein, is a communication protocol for sharing divided portions of information such that the sender is unaware of which portions were transferred to the receiver. In a "1-out-of-2" oblivious transfer, for example, a first participant is unaware of which of its two portions of random shares were transferred to a second participant. In addition, the second participant is only able to receive one of the portions of random shares of the first participant.

To facilitate processing of the retained random shares and received random shares at participant $104_1$ and participant $104_N$, a Beaver triple is generated by participant $104_K$ (operation 410). A Beaver triple, as used herein, is a multiplicative triple (e.g., <a, b,c>) used to perform arithmetic (e.g., multiplications) on secret or private data inputs. More specifically, a Beaver triple comprises two random factors a and b that are used to obfuscate sets of data inputs (e.g., by subtracting a or b from the data inputs) and whose product c=a·b is used to perform computations (e.g., multiplication, dot product, etc.) over the obfuscated data inputs.

A set of random triples are then generated based at least in part on the Beaver triple (operation 411). While derived from a Beaver triple, the random triples may not be Beaver triples. For example, consider a Beaver triple <9,2,18> that is generated at participant $104_K$. As can be observed, this triple is consistent with the Beaver triple property in that the third factor of the triple is the product of the first and second factors. Now consider a first random triple <7,1,3> that is generated and a second random triple <2,1,15> that is determined from the difference between the Beaver triple and the first random triple. In this case, neither of the random triples comply with the Beaver triple property requiring that the third factor of the triple is the product of the first and second factors. When the random triples are generated, the factors comprising the first random triple and the second random triple are shared with the computation participants (message 412 and message 413).

Each of the participants compute the differences between the retained random shares, received random shares, and respective random triple factors (operation 414 and operation 415). As an example, each participant might subtract a first random triple factor (e.g., factor a') from the random shares received from the other participant to determine a first difference, and subtract a second random triple factor (e.g., factor b') from the random shares retained by the participant to determine a second difference. The computed differences at each participant are then shared with the other participant (message $416_1$ and message $416_N$).

A dot product is then computed by each participant using the respective differences, random triple products (e.g., product c'), random shares, and/or other information at each participant (operation 418 and operation 419). At this stage, the dot products computed by the participants have no discernable meaning when taken individually, but can produce a meaningful result if combined. To control the disclosure of such open computation results, a neutral entity (e.g., third participant, secure enclave, etc.) may be implemented to perform the final computation(s). In privacy-preserving computation technique 400, participant $104_K$ performs this role by receiving the dot products computed by participant $104_1$ and participant $104_N$ (message $420_1$ and message $420_N$). The dot products are combined (e.g., summed) to determine a computation result (operation 422). Determination of the computation result is facilitated at least in part by the fact that the random triples used to determine the respective dot products at participant $104_1$ and participant $104_N$ were based at least in part on a single Beaver triple. The computation result can then be accessed by any authorized participant.

Throughout the privacy-preserving computation technique 400, the data sets from each participant in a particular computation are protected (e.g., privacy of the data sets is preserved) as long as there is no collusion between any of the participants. However, there is no protection against a participant who intentionally or unintentionally provides false or incorrect or incomplete information. In this case, a mechanism for verifying the computation results and/or underlying data is needed.

The foregoing discussions include techniques for verifying the integrity of the computation results and/or the data sets underlying the computation results (e.g., verification operations 230 of FIG. 2), which techniques and data are disclosed in further detail as follows.

Figure 5:
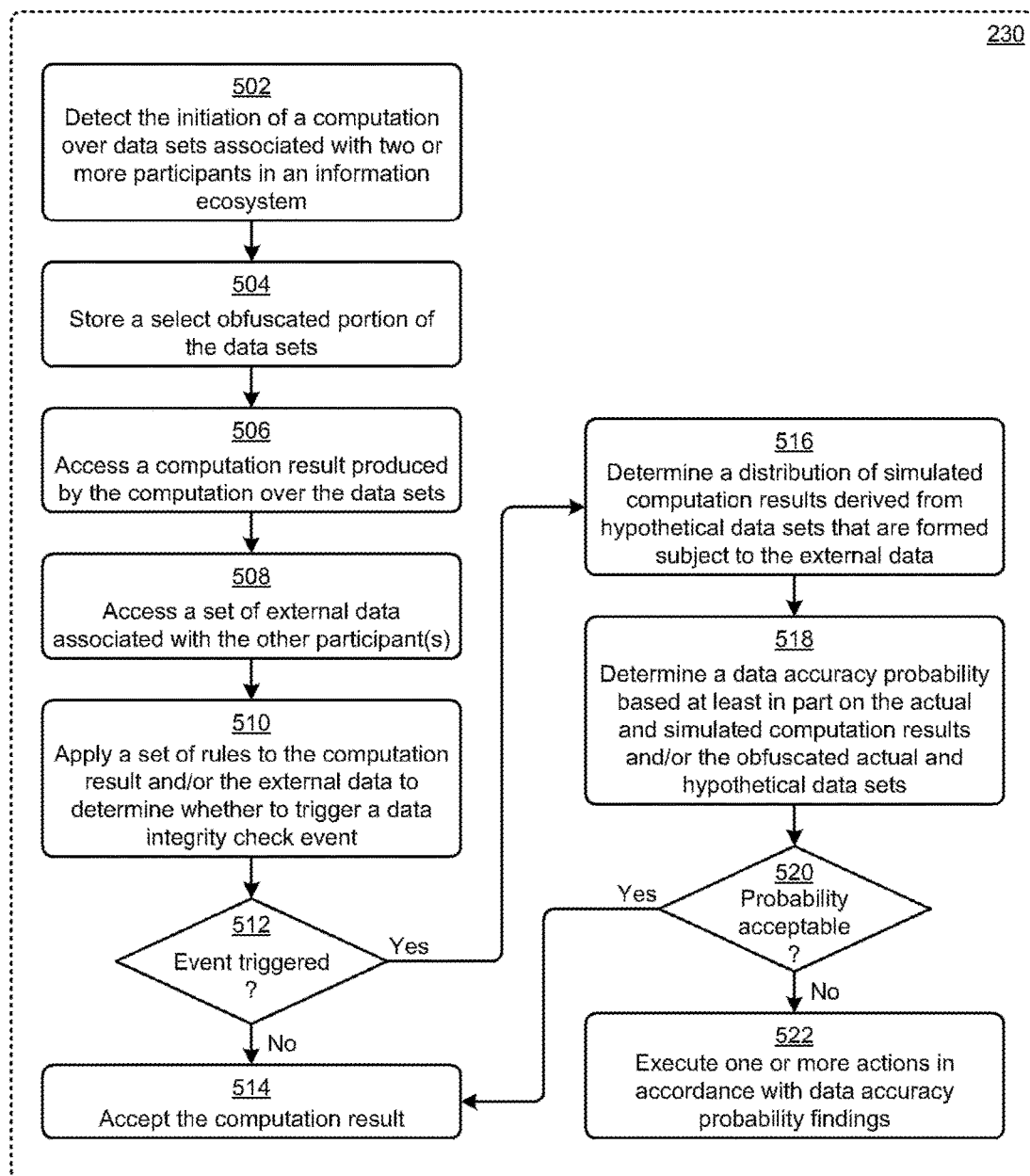
FIG. 5 depicts a private data verification technique as implemented in systems that verify data accuracy in privacy-preserving computations, according to an embodiment.

FIG. 5 depicts a private data verification technique 500 as implemented in systems that verify data accuracy in privacy-preserving computations. As an option, one or more variations of private data verification technique 500 or any aspect thereof may be implemented in the context of the architecture and functionality of the embodiments described herein. The private data verification technique 500 or any aspect thereof may be implemented in any environment.

FIG. 5 illustrates aspects pertaining to implementing a framework for performing computations over sets of data from two or more participants while preserving data privacy and participant accountability. Specifically, the figure is presented to illustrate one embodiment of certain steps and/or operations that facilitate verifying the integrity of the computation results and/or the data sets underlying the computation results of multi-participant privacy-preserving computations (e.g., verification operations 230 of FIG. 2).

Private data verification technique 500 commences by detecting the initiation of a computation over data sets associated with two or more participants in an information ecosystem (step 502). In the context considered herein, the computation is to be performed over the data sets of the participants while preserving the privacy of the data sets. A certain obfuscated portion of the data sets underlying the computation is stored (step 504). For example, a hash of one or more vectors used in the computation might be stored. In most cases, the obfuscation method (e.g., hash function) used to obfuscate the data might be known, but a means for reversing the hash is not provided so as to preserve the privacy of the underlying data. The computation result produced by the computation over the data sets is accessed (step 506). Certain sets of external data associated with other participant(s) may also be accessed by each participant (step 508).

For any participant with access to the computation result, a set of rules is applied to the computation result and/or the external data to determine whether to trigger a data integrity check event (step 510). A set of rules (e.g., rule base) such as data integrity rules 316 of FIG. 3 or any other rules described herein, comprises data records storing various information that can be used to form one or more constraints to apply to certain functions and/or operations. For example, the information pertaining to a rule in the rule base might comprise the conditional logic operands (e.g., input variables, conditions, constraints, etc.) and/or operators (e.g., "if", "then", "and", "or", "greater than", "less than", etc.) for forming a conditional logic statement that returns one or more results. More specifically, a rule might be applied to a computation result that triggers a data integrity check event if the computation result is below a certain threshold. Another rule might trigger a data integrity check event if the computation result is below a first threshold and a certain external data value is above a second threshold. In some cases, a data integrity check event is automatically triggered when a computation is completed.

If no data integrity check event is triggered ("No" path of decision 512), then the computation result is accepted (step 514). If a data integrity check event is triggered ("Yes" path of decision 512), then the participant with access to the computation result determines a distribution of simulated computation results derived from hypothetical data sets that are formed subject to the external data (step 516). Even with no knowledge of the underlying data used to produce the actual computation result, such simulated computation results can be derived, for example, with knowledge of the computation algorithm. As an example, the external data accessed by the participant might indicate that a certain data input value in a computation data set is to be set to "28". In this case, various hypothetical data sets that comprise combinations of data inputs that have at least one data input fixed at "28" are formed and used to determine the distribution of simulated computation results.

A data accuracy probability is then determined based at least in part on the actual computation result, the simulated computation result, the select obfuscated portion of the data sets, and/or the hypothetical data sets (step 518). In one scenario, the actual computation result may fall within the distribution of simulated computation results. In this case, the hypothetical data set that is associated with the simulated computation result that is equivalent to the actual computation result is obfuscated using the same obfuscation method (e.g., hash function) applied to the select obfuscated portion of the earlier stored data sets. If the two sets of obfuscated data (e.g., two hash values) match, then the data accuracy probability is 100%. If the hashes of the hypothetical data set and actual data set do not match, or the actual computation result does not fall within the simulated computation result distribution, then the data accuracy probability will be less than 100%. The value of the data accuracy probability when there is not a perfect match can be determined using various techniques (e.g., machine learning).

The data accuracy probability determined in step 518 is then checked (e.g., compared to a threshold) for acceptability. If the data accuracy probability is acceptable ("Yes" path of decision 520), then the computation result is accepted (step 514). If the data accuracy probability is not acceptable ("No" path of decision 520), then one or more actions are taken in accordance with the data accuracy probability findings (step 522). For example, a message might be sent to a suspect participant asking for a new set of data (e.g., a new questionnaire requesting new responses) or a message might be sent to a suspect participant denying a request associated with the computation.

An application of the various techniques disclosed herein for executing and verifying multi-participant privacy-preserving computations are described in detail in the following.

Figure 6:
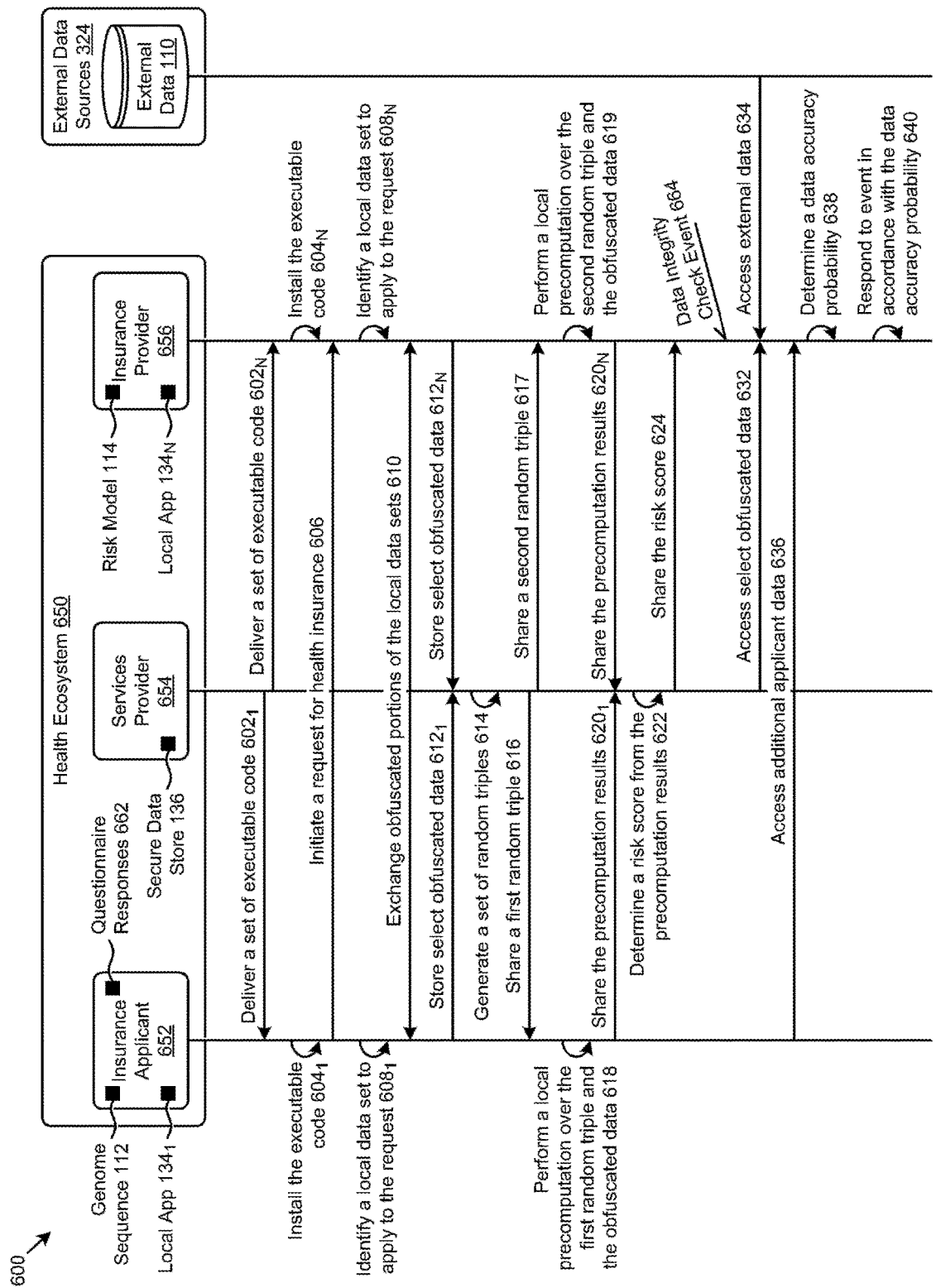
FIG. 6 depicts a private data verification scenario as implemented in systems that verify data accuracy in privacy-preserving computations, according to an embodiment.

FIG. 6 depicts a private data verification scenario 600 as implemented in systems that verify data accuracy in privacy-preserving computations. As an option, one or more variations of private data verification scenario 600 or any aspect thereof may be implemented in the context of the architecture and functionality of the embodiments described herein. The private data verification scenario 600 or any aspect thereof may be implemented in any environment.

FIG. 6 illustrates aspects pertaining to implementing a framework for performing computations over sets of data from two or more participants while preserving data privacy and participant accountability. Specifically, the figure is being presented to illustrate a representative multi-participant privacy-preserving computation scenario in which a quantitative measurement of the integrity of computation results and/or data sets underlying the computation results is determined according to the herein disclosed techniques. More specifically, the private data verification scenario 600 illustrates a privacy-preserving computation carried out in a health ecosystem 650 by an insurance applicant 652 and an insurance provider 656 with support from a services provider 654.

Private data verification scenario 600 commences with insurance applicant 652 and insurance provider 656 receiving respective sets of executable code (e.g., applications or apps) delivered by services provider 654 (message $602_1$ and message $602_N$). Each of the participants receiving the executable code installs the code as applications (e.g., local app 134₁ and local app 134$_N$) on one or more computing devices associated with the participants (operation 604₁ and operation 604$_N$). The participants can then interact with the applications to facilitate at least some aspects of the techniques implemented to carry out the private data verification scenario 600. Specifically, insurance applicant 652 might interact with local app 134₁ to initiate a request for health insurance from insurance provider 656 (message 606).

To serve the foregoing request, insurance applicant 652 and insurance provider 656 identify a local data set to apply to the request (operation 608₁ and operation 608$_N$). For example, insurance applicant 652 might identify a genome sequence 112 and a set of questionnaire responses 662 to apply to the request, and insurance provider 656 might identify a risk model 114 to apply to the request. The participants then exchange obfuscated portions of their respective data sets with each other (message 610). As merely one example, the participants might implement the techniques discussed as pertains to FIG. 4 to exchange random shares of their local data. As shown, services provider 654 might also store (e.g., in secure data store 136) select portions of the obfuscated data from one or both participants (message 612₁ and message 612$_N$).

To facilitate precomputations over the exchanged obfuscated data at insurance applicant 652 and insurance provider 656, a set of random triples are generated by services provider 654 (operation 614). As earlier described, the random triples might be derived from a Beaver triple generated by services provider 654. A respective one of the random triples are then shared with the participants (message 616 and message 617). Each of the participants access their respective random triple to perform one or more precomputations over the obfuscated data that they have received and/or data that they own (operation 618 and operation 619). The precomputation results from each participant are shared with services provider 654 (message 620₁ and message 620$_N$), which precomputation results the services provider 654 uses to determine a risk score associated with the aforementioned request for health insurance (operation 622). The risk score is then shared with insurance provider 656, who is authorized to view the computation result (message 624).

If a data integrity check event 664 that is associated with the risk score is triggered and detected at insurance provider 656, the select obfuscated data earlier stored at services provider 654 is accessed (message 632). Insurance provider 656 may also access certain sets of external data 110 from external data sources 324 in response to data integrity check event 664 (message 634). In some cases, additional data (e.g., a new instance of questionnaire responses 662) may also be requested and accessed by insurance provider 656 (message 636).

Strictly as one example, an insurance provider 656 may access online activity records (e.g., shopping site activity) at external data sources 324, then use the online information in the online activity records to calculate a data accuracy probability. Continuing this example, consider the case where an insurance provider accesses online shopping records, and in doing so determines that the insurance applicant has purchased "size XX-Large" underwear at the online shopping site. That online information (e.g., occurrence of a sales record that indicates that the insurance applicant had purchased "size XX-Large" underwear) can be used to calculate a data accuracy probability. For example, if the insurance applicant had indicated a height of 5'11" and a weight of 150 pounds, the purchase by the applicant of "size XX-Large" underwear might cast suspicion that the applicant's indicated height of 5'11" and a weight of 150 pounds is truthful.

In some cases, many online activity records at external data sources 324 are accessed to retrieve many instances of online information, portions of which online information is, in turn, used to calculate a data accuracy probability.

Using the foregoing information and/or other information, a data accuracy probability is determined by insurance provider 656 (operation 638). Insurance provider 656 then responds to data integrity check event 664 in accordance with the data accuracy probability (operation 640). For example, if the risk score and the data accuracy probability is acceptable, insurance provider 656 may respond by underwriting and pricing an insurance policy for insurance applicant 652. For another combination of risk score and/or data accuracy probability, insurance provider 656 may deny insurance, request more information, and/or take some other action.

Additional Embodiments of the Disclosure

Additional Practical Application Examples

Figure 7A:
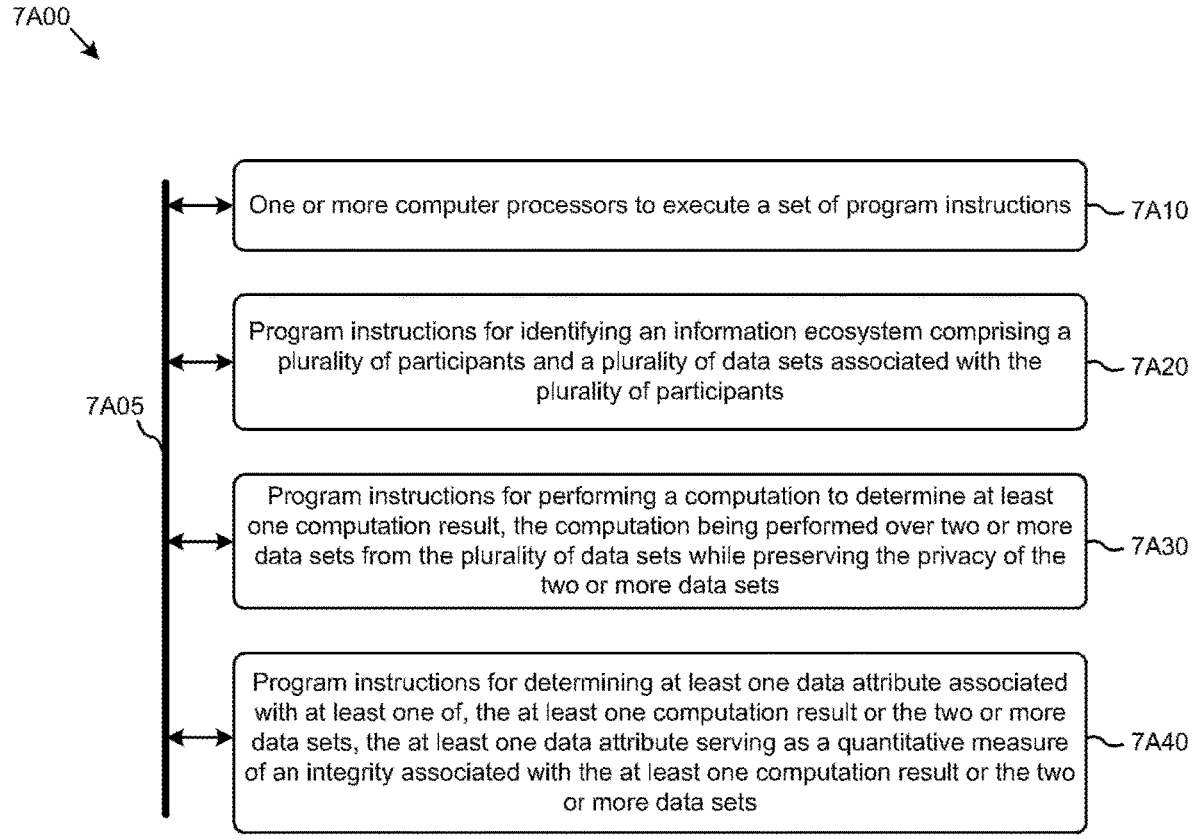
FIG. 7A depicts system components as arrangements of computing modules that are interconnected so as to implement certain of the herein-disclosed embodiments.

FIG. 7A depicts a system 7A00 as an arrangement of computing modules that are interconnected so as to operate cooperatively to implement certain of the herein-disclosed embodiments. This and other embodiments present particular arrangements of elements that, individually or as combined, serve to form improved technological processes that address a lack of transparency of the underlying data in privacy-preserving computations. The partitioning of system 7A00 is merely illustrative and other partitions are possible. As an option, the system 7A00 may be implemented in the context of the architecture and functionality of the embodiments described herein. Of course, however, the system 7A00 or any operation therein may be carried out in any desired environment.

The system 7A00 comprises at least one processor and at least one memory, the memory serving to store program instructions corresponding to the operations of the system. As shown, an operation can be implemented in whole or in part using program instructions accessible by a module. The modules are connected to a communication path 7A05, and any operation can communicate with any other operations over communication path 7A05. The modules of the system can, individually or in combination, perform method operations within system 7A00. Any operations performed within system 7A00 may be performed in any order unless as may be specified in the claims.

The shown embodiment implements a portion of a computer system, presented as system 7A00, comprising one or more computer processors to execute a set of program code instructions (module 7A10) and modules for accessing memory to hold program code instructions to perform: identifying an information ecosystem comprising a plurality of participants and a plurality of data sets associated with the plurality of participants (module 7A20); performing a computation to determine at least one computation result, the computation being performed over two or more data sets from the plurality of data sets while preserving the privacy of the two or more data sets (module 7A30); and determining at least one data attribute associated with at least one of, the at least one computation result or the two or more data sets, the at least one data attribute serving as a quantitative measure of an integrity associated with the at least one computation result or the two or more data sets (module 7A40).

Variations of the foregoing may include more or fewer of the shown modules. Certain variations may perform more or fewer (or different) steps and/or certain variations may use data elements in more, or in fewer, or in different operations.

Still further, some embodiments include variations in the operations performed, and some embodiments include variations of aspects of the data elements used in the operations. As one particular example, consider a scenario where two or more participants (e.g., a patient, a physician, a genomics sequencing firm, etc.) want to privately exchange a respective two or more data sets of sensitive information to be used to achieve a particular computation result (e.g., a diagnosis, a health risk estimation). In this scenario, each of the participants want to protect their sensitive information. For example, a patient might want to protect his or her "smoking status", a physician and/or a genomics sequencing entity might want to protect their know-how about how a diagnosis is reached and/or how genomics sequencing is performed, etc. In such a scenario, sharing of secrets, as well as generation and sharing of Beaver triples and/or other arithmetic triples, can be employed so as to facilitate computations to produce particular computation results while still observing complete privacy of the information. A system that operates in this scenario to perform estimation of a particular user's risk for cardiovascular disease while still observing complete privacy of shared information is shown and described as pertains to FIG. 7B.

Figure 7B:
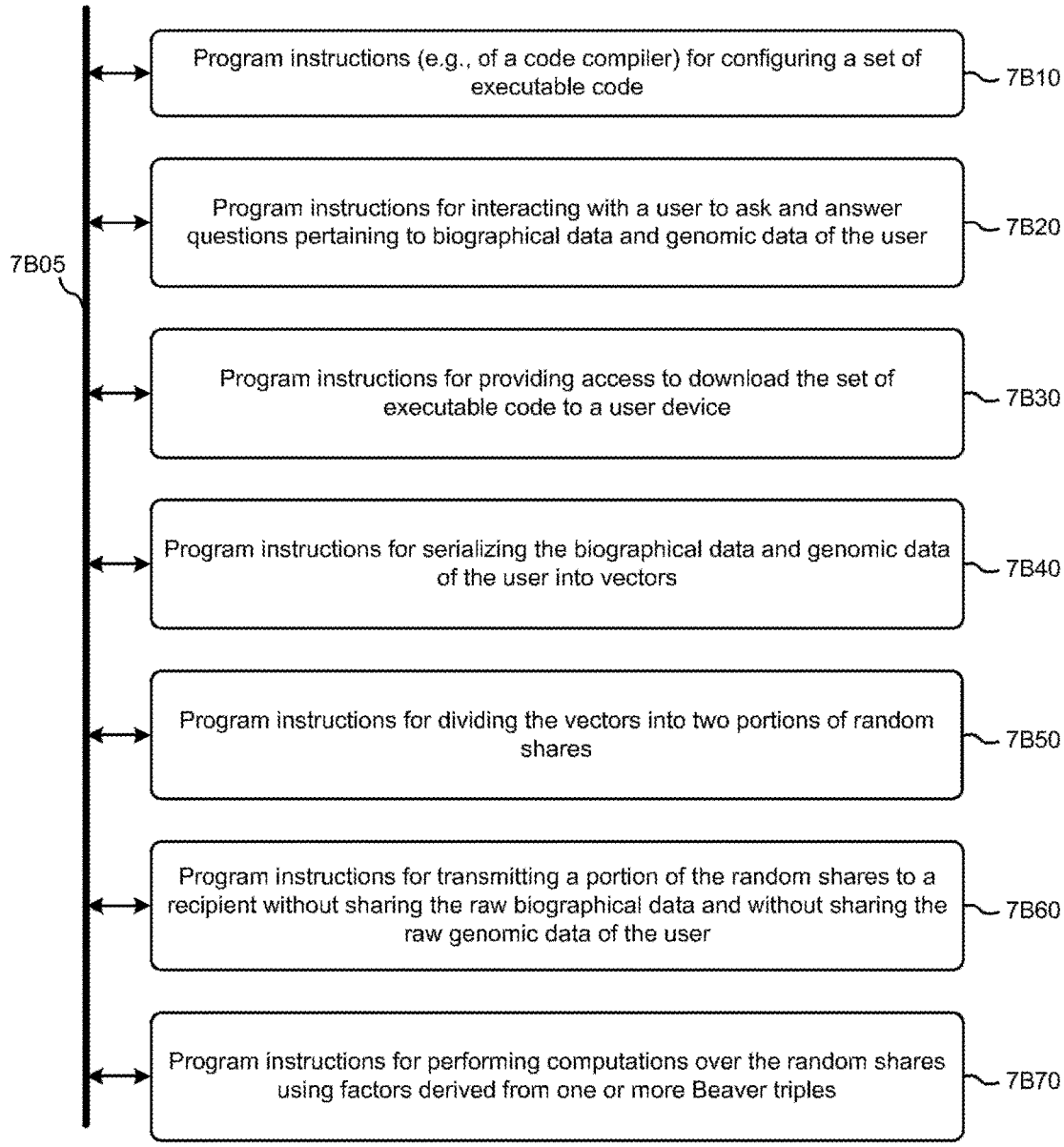
FIG. 7B depicts components as arrangements of computing modules that are interconnected so as to implement a system for private exchange of two or more data sets of sensitive information, according to an embodiment.

FIG. 7B depicts a system 7B00 as an arrangement of computing modules that are interconnected so as to operate cooperatively to implement private exchange of two or more data sets of sensitive information.

The system 7B00 comprises at least one processor and at least one memory, the memory serving to store program instructions corresponding to the operations of the system. As shown, an operation can be implemented in whole or in part using program instructions accessible by a module. The modules are connected to a communication path 7B05, and any operation can communicate with any other operations over communication path 7B05. The modules of the system can, individually or in combination, perform method operations within system 7B00. Any operations performed within system 7B00 may be performed in any order unless as may be specified in the claims.

The shown embodiment implements a portion of a computer system, presented as system 7B00, comprising one or more computer processors to execute a set of program code instructions. The partitioning of system 7B00 is merely illustrative and other partitions are possible. As shown, system 7B00 implements a method that supports estimation of a particular user's risk for cardiovascular disease (CVD). The estimation of the user's risk for cardiovascular disease is made by a genomics company using privacy-preserving computations that are facilitated by a third party. Estimation of CVD involves computations over private information such as the user's gender, the user's age, his/her body mass index (BMI), his/her cholesterol (e.g., HDL, LDL) levels, as well as the presence/absence of genomic risk factors. Such genomic risk factors are often based, at least in part, on the individual's genome sequence.

The foregoing information is applied to a specialized risk model developed and/or owned by the genomics company to produce a genetic risk score (e.g., metaGRS). Even though the foregoing biographical and genomic data is used in the estimation of a user's risk of cardiovascular disease, the estimate is computed without requiring the user to share his or her raw biographical data and without requiring the user to share his or her raw genomic data.

Specifically, the privacy-preserving computations involved in the estimation are facilitated by an application or app that can be downloaded to a user device. After downloading the application or app, the user responds to questions of a questionnaire (e.g., age, BMI, etc.) and authorizes the application or app to access the user's genome sequence. The application or app does not transmit the raw questionnaire data and/or the raw genome sequence to the genomic company. Instead, the application or app shares only obfuscated vectors, factors, random values and other secrets with the genomics company.

In some scenarios, additional information and/or biomaterials, such as a blood sample from which additional information can be derived, is shared anonymously. After the genomics company analyzes additional information and/or biomaterials, and after the genomics company completes sequencing of the obfuscated vectors, factors, random values, and other secrets pertaining to the user's DNA, the genomics company uses further obfuscated vectors, factors, random values, and other secrets to securely compute and share the results of the blood and genome analysis with the user. The user's CVD risk and other information (e.g., suggested risk-reduction steps) are displayed to the user. Only the particular user has access to his or her CVD risk and other information.

Mechanisms for accomplishing the foregoing estimation of a user's risk of cardiovascular disease without requiring the user to share his or her raw biographical data and raw genomic data can be implemented by a set of cooperatively interconnected modules. Such a set of cooperatively interconnected modules is depicted in FIG. 7B as system 7B00.

Specifically, and as shown, a set of executable code is configured (module 7B10) such that, when executed, the executable code interacts with a user to ask and receive the user's answers pertaining to biographical data and genomic data of the user (module 7B20). Execution of the executable code further serves for: providing access to download the set of executable code to a user device (module 7B30); serializing the biographical data and genomic data of the user into vectors (module 7B40); dividing the vectors into two portions of random shares (module 7B50); transmitting only a portion of the random shares to a recipient without sharing the raw biographical and genomic data of the user (module 7B60); and performing computations over the random shares using factors derived from one or more Beaver triples (module 7B70).

Using variations of the foregoing steps, (e.g., using obfuscated vectors, factors, random values, and other secrets) the genomics company can securely determine and share the results of the blood and genome analysis with the user in a manner such that only the particular user has access to his or her CVD risk and other information.

Figure 7C:
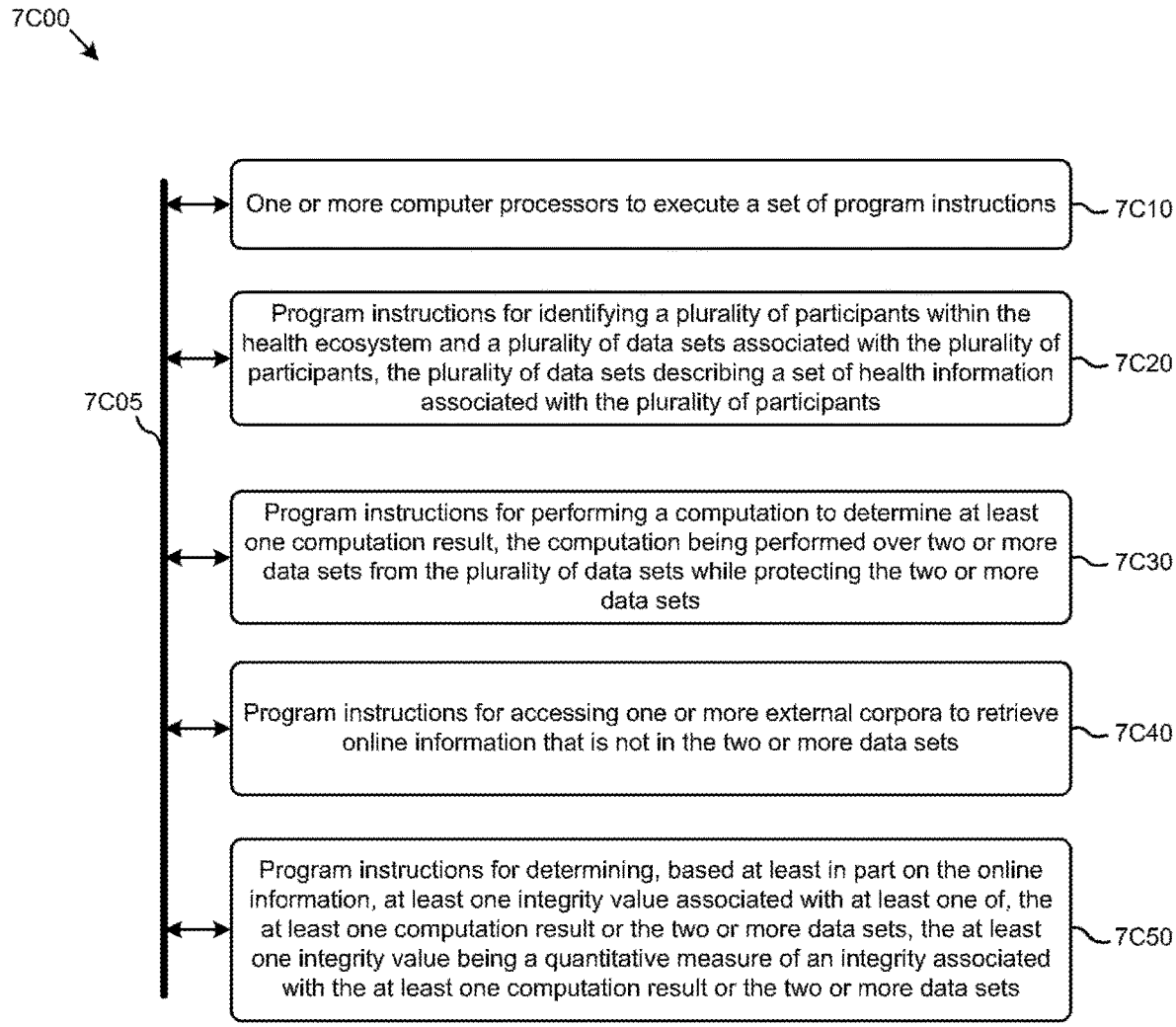
FIG. 7C depicts components as arrangements of computing modules that are interconnected so as to implement a system for verifying data accuracy in privacy-preserving computations in a health ecosystem, according to an embodiment.

FIG. 7C depicts components as arrangements of computing modules that are interconnected so as to implement a system for verifying data accuracy in privacy-preserving computations in a health ecosystem. The shown system 7C00 as an arrangement of computing modules that are interconnected so as to operate cooperatively to implement certain of the herein-disclosed embodiments.

This and other embodiments present particular arrangements of elements that, individually or as combined, serve to form improved technological processes that address a lack of transparency of the underlying data in privacy-preserving computations. The partitioning of system 7C00 is merely illustrative and other partitions are possible. As an option, the system 7C00 may be implemented in the context of the architecture and functionality of the embodiments described herein. Of course, however, the system 7C00 or any operation therein may be carried out in any desired environment.

The system 7C00 comprises at least one processor and at least one memory, the memory serving to store program instructions corresponding to the operations of the system. As shown, an operation can be implemented in whole or in part using program instructions accessible by a module. The modules are connected to a communication path 7C05, and any operation can communicate with any other operations over communication path 7C05. The modules of the system can, individually or in combination, perform method operations within system 7C00. Any operations performed within system 7C00 may be performed in any order unless as may be specified in the claims.

The shown embodiment implements a portion of a computer system, presented as system 7C00, comprising one or more computer processors to execute a set of program code instructions (module 7C10) and modules for accessing memory to hold program code instructions to perform: identifying a plurality of participants within the health ecosystem and a plurality of data sets associated with the plurality of participants, the plurality of data sets describing a set of health information associated with the plurality of participants (module 7C20); performing a computation to determine at least one computation result, the computation being performed over two or more data sets from the plurality of data sets while protecting the two or more data sets (module 7C30); accessing one or more external corpora to retrieve online information that is not in the two or more data sets (module 7C40); and determining, based at least in part on the online information, at least one integrity value associated with at least one of, the at least one computation result or the two or more data sets, the at least one integrity value being a quantitative measure of a level of integrity associated with the at least one computation result or the two or more data sets (module 7C50).

Variations of the foregoing may include more or fewer of the shown modules. Certain variations may perform more or fewer (or different) steps and/or certain variations may use data elements in more, or in fewer, or in different operations.

System Architecture Overview

Additional System Architecture Examples

Figure 8A:
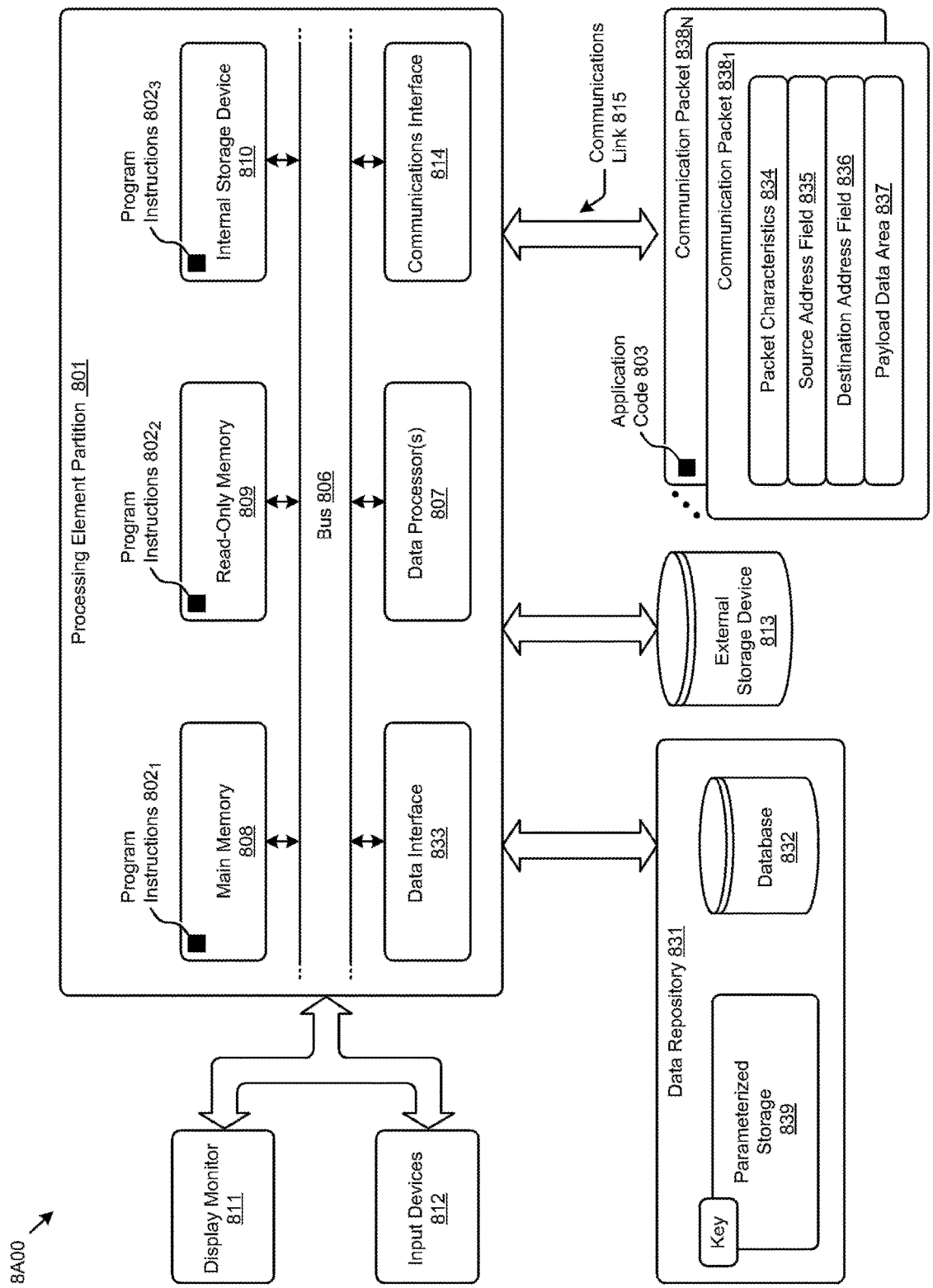
FIG. 8A and FIG. 8B present block diagrams of computer system architectures having components suitable for implementing embodiments of the present disclosure, and/or for use in the herein-described environments.

FIG. 8A depicts a block diagram of an instance of a computer system 8A00 suitable for implementing embodiments of the present disclosure. Computer system 8A00 includes a bus 806 or other communication mechanism for communicating information. The bus interconnects subsystems and devices such as a central processing unit (CPU), or a multi-core CPU (e.g., data processor 807), a system memory (e.g., main memory 808, or an area of random access memory (RAM)), a non-volatile storage device or non-volatile storage area (e.g., read-only memory 809), an internal storage device 810 or external storage device 813 (e.g., magnetic or optical), a data interface 833, a communications interface 814 (e.g., PHY, MAC, Ethernet interface, modem, etc.). The aforementioned components are shown within processing element partition 801, however other partitions are possible. Computer system 8A00 further comprises a display 811 (e.g., CRT or LCD), various input devices 812 (e.g., keyboard, cursor control), and a data repository 831.

According to an embodiment of the disclosure, computer system 8A00 performs specific operations by data processor 807 executing one or more sequences of one or more program instructions contained in a memory. Such instructions (e.g., program instructions $802_1$, program instructions $802_2$, program instructions $802_3$, etc.) can be contained in or can be read into a storage location or memory from any computer readable/usable storage medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination thereof.

According to an embodiment of the disclosure, computer system 8A00 performs specific networking operations using one or more instances of communications interface 814. Instances of communications interface 814 may comprise one or more networking ports that are configurable (e.g., pertaining to speed, protocol, physical layer characteristics, media access characteristics, etc.) and any particular instance of communications interface 814 or port thereto can be configured differently from any other particular instance. Portions of a communication protocol can be carried out in whole or in part by any instance of communications interface 814, and data (e.g., packets, data structures, bit fields, etc.) can be positioned in storage locations within communications interface 814, or within system memory, and such data can be accessed (e.g., using random access addressing, or using direct memory access DMA, etc.) by devices such as data processor 807.

Communications link 815 can be configured to transmit (e.g., send, receive, signal, etc.) any types of communications packets (e.g., communication packet $838_1$, communication packet $838_N$) comprising any organization of data items. The data items can comprise a payload data area 837, a destination address 836 (e.g., a destination IP address), a source address 835 (e.g., a source IP address), and can include various encodings or formatting of bit fields to populate packet characteristics 834. In some cases, the packet characteristics include a version identifier, a packet or payload length, a traffic class, a flow label, etc. In some cases, payload data area 837 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 807 for execution. Such a medium may take many forms including, but not limited to, non-volatile media and volatile media. Non-volatile media includes, for example, optical or magnetic disks such as disk drives or tape drives. Volatile media includes dynamic memory such as RAM.

Common forms of computer readable media include, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of data repository 831, which in turn can be formatted into any one or more storage areas, and which can comprise parameterized storage 839 accessible by a key (e.g., filename, table name, block address, offset address, etc.).

Execution of the sequences of instructions to practice certain embodiments of the disclosure are performed by a single instance of a computer system 8A00. According to certain embodiments of the disclosure, two or more instances of computer system 8A00 coupled by a communications link 815 (e.g., LAN, public switched telephone network, or wireless network) may perform the sequence of instructions required to practice embodiments of the disclosure using two or more instances of components of computer system 8A00.

Computer system 8A00 may transmit and receive messages such as data and/or instructions organized into a data structure (e.g., communications packets). The data structure can include program instructions (e.g., application code 803), communicated through communications link 815 and communications interface 814. Received program instructions may be executed by data processor 807 as it is received and/or stored in the shown storage device or in or upon any other non-volatile storage for later execution. Computer system 8A00 may communicate through a data interface 833 to a database 832 on a data repository 831. Data items in a database can be accessed using a primary key (e.g., a relational database primary key).

Processing element partition 801 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 807. Some embodiments include one or more special-purpose hardware components (e.g., power control, logic, sensors, transducers, etc.). Some embodiments of a module include instructions that are stored in a memory for execution so as to facilitate operational and/or performance characteristics pertaining to verifying data accuracy in privacy-preserving computations. A module may include one or more state machines and/or combinational logic used to implement or facilitate the operational and/or performance characteristics pertaining to verifying data accuracy in privacy-preserving computations.

Various implementations of database 832 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of verifying data accuracy in privacy-preserving computations). Such files, records, or data structures can be brought into and/or stored in volatile or non-volatile memory. More specifically, the occurrence and organization of the foregoing files, records, and data structures improve the way that the computer stores and retrieves data in memory, for example, to improve the way data is accessed when the computer is performing operations pertaining to verifying data accuracy in privacy-preserving computations, and/or for improving the way data is manipulated when performing computations over sets of data from two or more participants while preserving data privacy and participant accountability.

Figure 8B:
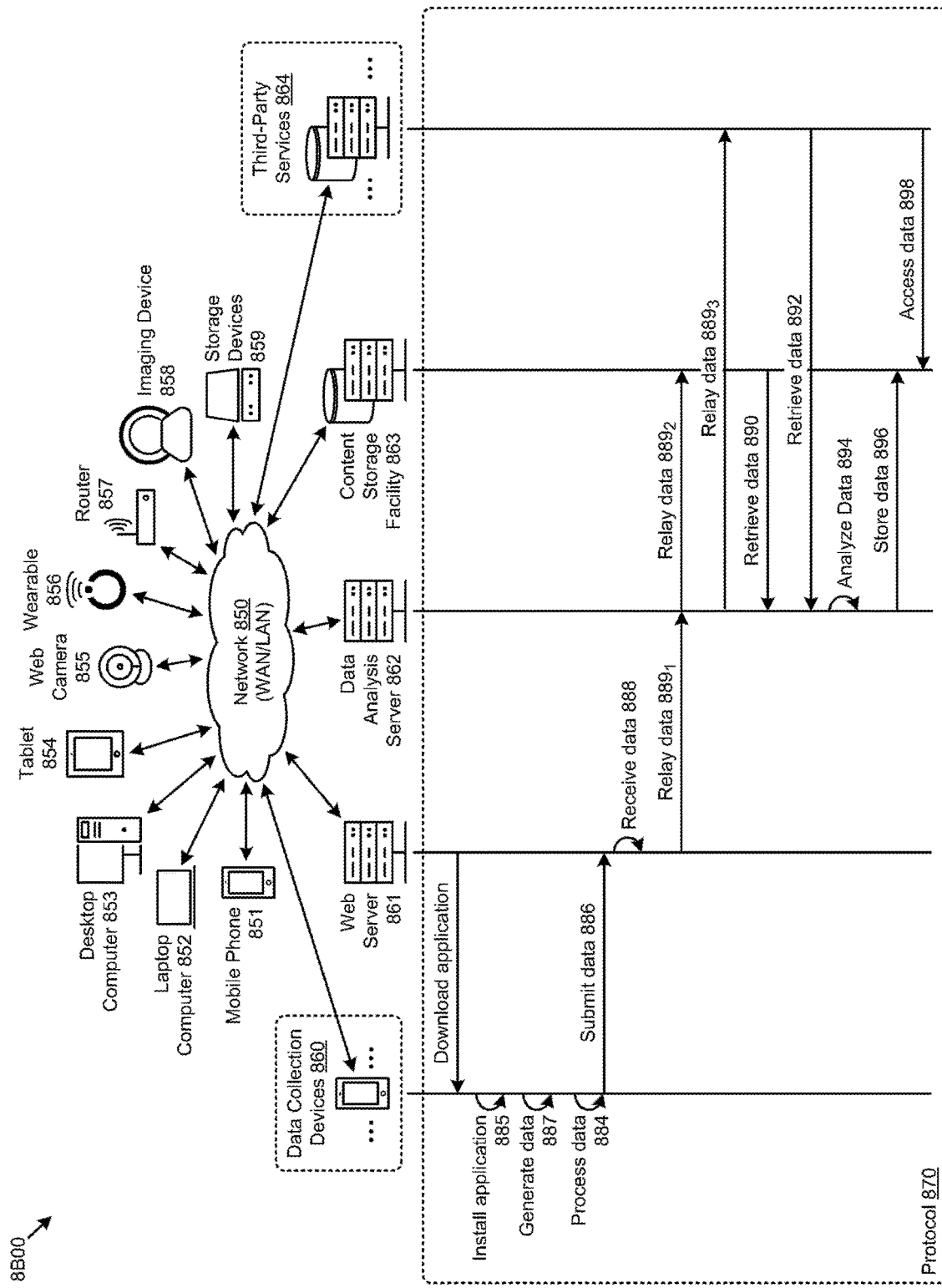

FIG. 8B depicts an environment 8B00 in which embodiments of the present disclosure can operate. As an option, one or more aspects shown in environment 8B00 or any combination of components of the environment may be implemented in the context of the architecture and functionality of the embodiments described herein.

As shown environment 8B00 comprises various computing systems (e.g., servers and devices) interconnected by a network 850. The network 850 can comprise any combination of a wide area network (e.g., WAN), local area network (e.g., LAN), cellular network, wireless LAN (e.g., WLAN), or any such means for enabling communication of computing systems. The network 850 can also be referred to as "the Internet" or as an "Internet". The example environment 8B00 comprises data collection devices 860, an instance of a web server 861, an instance of a data analysis server 862, a content storage facility 863, and optional instances of third-party services 864, which third-party services 864 may communicate with any other the other operational element over a network.

The servers and devices shown in environment 8B00 can represent any single computing system with dedicated hardware and software, or the servers and devices shown in environment 8B00 can represent multiple computing systems connected together (e.g., in a server farm, or in a host farm, etc.). In some cases, multiple computing systems share resources. For example, the web server 861 and the data analysis server 862 might be closely coupled (e.g., co-located) and/or might be implemented using the same hardware platform.

The environment 8B00 further comprises a variety of other devices such as a mobile phone 851, a laptop 852, a desktop computer 853, a tablet 854, a web camera 855, and a wearable device 856 etc. The environment further comprises computing equipment such as a router 857, an imaging device 858 (e.g., CT scanner, MRI machine, etc.), and any number of storage devices 859, etc. Some or all of the foregoing computing devices and computing equipment may support software (e.g., a browser, mobile application, etc.) and hardware (e.g., an LCD display, a graphics processing unit, display, monitor, etc.) capable of processing and displaying information (e.g., an image, a web page, etc.). Any of the foregoing computing devices or computing equipment can serve as one of the data collection devices 860.

In some embodiments, any particular one of the data collection devices 860 can be used in conjunction with a different particular one of the data collection devices to determine the location and/or identity of a user.

As shown, the computing devices and computing equipment can perform a set of high-level interactions (e.g., operations, messages, etc.) in a protocol 870. Specifically, the protocol can represent interactions in systems for measuring the quality of user-provided information.

An application or app can be generated using any known techniques. Such an application or app cooperates with other operational elements of the environment to perform operations pertaining to verifying data accuracy in privacy-preserving computations, and/or to perform computerized operations pertaining to implementing a framework for performing computations over sets of data from two or more participants while preserving data privacy and participant accountability. The application or app may be configured so as to operate on any one or more data collection device. As shown, any of the data collection devices 860 can download such an application or app from web server 861 and install the application (operation 885). The application can be used to capture and/or generate data (operation 887), process the captured or generated data (operation 884), and submit data to the web server (message 886).

To perform one or more operations of protocol 870, the web server is configured to receive data (operation 888) corresponding to the data submitted from the data collection devices. Such received data may be relayed or otherwise transmitted (message $889_1$, or message $889_2$, or message $889_3$) to downstream computing equipment such as data analysis server 862, and/or to a content storage facility 863, and/or to any one or more third-party services 864. Furthermore, the data analysis server may retrieve data (message 890) from any storage facility, including from content storage facility 863 or any one or more of the third-party services (message 892).

An instance of a data analysis server 862 can be configured to autonomously (e.g., under program control) analyze any received data (message 894). Moreover, example instances of a data analysis server 862 can be configured to store data (message 896) at any storage facility, including at content storage facility 863 or any one or more storage devices of third-party services.

In some cases, the third-party services produce additional data that is derived, directly or indirectly, from the data received from the data collection devices. In some cases, and as shown, such additional data might be still further retrieved (message 898) and analyzed by data analysis server 862. As such, data can be transformed in a cascading fashion. Specifically, data can be initially processed at the data collection device, then alternatively or additionally, the resulting data can be processed at the data analysis server, then alternatively or additionally, the still further resulting data can be processed at the third-party services.

In the foregoing specification, the disclosure has been described with reference to specific embodiments thereof. It will however be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are to be regarded in an illustrative sense rather than in a restrictive sense.

What is claimed is:

1. A method for verifying privacy-preserving computations in an information ecosystem, the method comprising:
in an environment comprising a plurality of participants within the information ecosystem, wherein a plurality of data sets comprise at least a first data set of health information associated with a first one of the plurality of participants, and a second data set comprising a risk model associated with a second one of the plurality of participants, providing at least one application that is downloaded to a user device of the plurality of participants, wherein the at least one application is configured to divide at least a portion of the health information into obfuscated health information;
performing a privacy-preserving computation over the obfuscated health information by:
receiving, by the at least one application, a random triple from a computation manager, the random triple being based at least in part on a Beaver triple generated by the computation manager;
performing, by the at least one application, the privacy-preserving computation to determine at least one computation result, the privacy-preserving computation being performed over the obfuscated health information and based at least in part on the random triple; and
accessing, over a network, one or more external corpora to retrieve online information comprising at least one external data value that is not in the plurality of data sets, then triggering, by a computer, a data integrity check to determine an accuracy of the privacy-preserving computation based at least in part on the at least one external data value and requesting additional data when the accuracy is below a threshold.

2. The method of claim 1, wherein the plurality of participants comprises at least one of a user, a patient, a physician, an insurance applicant, an insurance provider, a genomics sequencing entity, a genomics company, or a pharmaceutical company, and wherein the first data set comprises at least one of a genome sequence or a set of questionnaire responses, and wherein the second data set describes a risk model.

3. The method of claim 1, further comprising:
determining at least one integrity value based at least in part on the data integrity check.

4. The method of claim 1, further comprising:
delivering at least one set of executable code to install at a respective at least one user device associated with the plurality of participants, the at least one set of executable code being delivered to facilitate carrying out at least a portion of the method.

5. The method of claim 1, wherein the data integrity check is based at least in part on a set of online activity records.

6. The method of claim 5, wherein the set of online activity records comprises shopping records.

7. The method of claim 1, wherein an integrity value is determined in response to triggering the data integrity check.

8. The method of claim 7, wherein the data integrity check is triggered by at least one of, access to external data, or application of one or more rules to the at least one computation result.

9. The method of claim 7, wherein the integrity value is a data accuracy probability.

10. A non-transitory computer readable medium having stored thereon a sequence of instructions which, when stored in memory and executed by a processor cause the processor to perform acts for verifying privacy-preserving computations in an information ecosystem, the acts comprising:
in an environment comprising a plurality of participants within the information ecosystem, wherein a plurality of data sets comprise at least a first data set of health information associated with a first one of the plurality of participants, and a second data set comprising a risk model associated with a second one of the plurality of participants, providing at least one application that is downloaded to a user device of the plurality of participants, wherein the at least one application is configured to divide at least a portion of the health information into obfuscated health information, and wherein the sequence of instructions comprise code for:

performing a privacy-preserving computation over the obfuscated health information by:

receiving, by the at least one application, a random triple from a computation manager, the random triple being based at least in part on a Beaver triple generated by the computation manager;

performing, by the at least one application, the privacy-preserving computation to determine at least one computation result, the privacy-preserving computation being performed over the obfuscated health information and based at least in part on the random triple; and accessing, over a network, one or more external corpora to retrieve online information comprising at least one external data value that is not in the plurality of data sets, then triggering, by a computer, a data integrity check to determine an accuracy of the privacy-preserving computation based at least in part on the at least one external data value and requesting additional data when the accuracy is below a threshold.

11. The non-transitory computer readable medium of claim 10, wherein the plurality of participants comprises at least one of a user, a patient, a physician, an insurance applicant, an insurance provider, a genomics sequencing entity, a genomics company, or a pharmaceutical company, and wherein the first data set comprises at least one of a genome sequence or a set of questionnaire responses, and wherein the second data set describes a risk model.

12. The non-transitory computer readable medium of claim 10, further comprising instructions which, when stored in memory and executed by the processor cause the processor to perform further acts of:

determining at least one integrity value based at least in part on the data integrity check.

13. The non-transitory computer readable medium of claim 10, further comprising instructions which, when stored in memory and executed by the processor cause the processor to perform further acts of:

delivering at least one set of executable code to install at a respective at least one user device associated with the plurality of participants.

14. The non-transitory computer readable medium of claim 10, wherein the data integrity check is based at least in part on a set of online activity records.

15. The non-transitory computer readable medium of claim 14, wherein the set of online activity records comprises shopping records.

16. The non-transitory computer readable medium of claim 10, wherein an integrity value is determined in response to triggering the data integrity check.

17. The non-transitory computer readable medium of claim 16, wherein the data integrity check is triggered by at least one of, access to external data, or application of one or more rules to the at least one computation result.

18. The non-transitory computer readable medium of claim 16, wherein the integrity value is a data accuracy probability.

19. A system for verifying privacy-preserving computations in an information ecosystem, the system comprising:

a storage medium having stored thereon a sequence of instructions; and a processor that executes the sequence of instructions to cause the processor to perform acts comprising, in an environment comprising a plurality of participants within the information ecosystem, wherein a plurality of data sets comprise at least a first data set of health information associated with a first one of the plurality of participants, and a second data set comprising a risk model associated with a second one of the plurality of participants, providing at least one application that is downloaded to a user device of the plurality of participants, wherein the at least one application is configured to divide at least a portion of the health information into obfuscated health information, and wherein the sequence of instructions comprise code for:

performing a privacy-preserving computation over the obfuscated health information by:

receiving, by the at least one application, a random triple from a computation manager, the random triple being based at least in part on a Beaver triple generated by the computation manager;

performing, by the at least one application, the privacy-preserving computation to determine at least one computation result, the privacy-preserving computation being performed over the obfuscated health information and based at least in part on the random triple; and accessing, over a network, one or more external corpora to retrieve online information comprising at least one external data value that is not in the plurality of data sets, then triggering, by a computer, a data integrity check to determine an accuracy of the privacy-preserving computation based at least in part on the at least one external data value and requesting additional data when the accuracy is below a threshold.

20. The system of claim 19, wherein the plurality of participants comprises at least one of a user, a patient, a physician, an insurance applicant, an insurance provider, a genomics sequencing entity, a genomics company, or a pharmaceutical company, and wherein the first data set comprises at least one of a genome sequence or a set of questionnaire responses, and wherein the second data set describes a risk model.

21. The system of claim 19, further comprising instructions which, when stored in memory and executed by the processor cause the processor to perform further acts of:

determining at least one integrity value based at least in part on the data integrity check.

22. The system of claim 19, further comprising instructions which, when stored in memory and executed by the processor cause the processor to perform further acts of:

delivering at least one set of executable code to install at a respective at least one user device associated with the plurality of participants.

23. The system of claim 19, wherein the data integrity check is based at least in part on a set of online activity records.

24. The system of claim 23, wherein the set of online activity records comprises shopping records.

25. The system of claim 19, wherein an integrity value is determined in response to triggering the data integrity check.

26. The system of claim 25, wherein the data integrity check is triggered by at least one of, access to external data, or application of one or more rules to the at least one computation result.

27. The system of claim 25, wherein the integrity value is a data accuracy probability.

28. A system for verifying privacy-preserving computations in an information ecosystem, the system comprising:
a storage medium having stored thereon a sequence of instructions; and
a processor that executes the sequence of instructions to cause the processor to perform acts comprising,
in an environment comprising a plurality of participants within the information ecosystem, wherein a plurality of data sets comprise at least a first data set of health information associated with a first one of the plurality of participants, and
a second data set comprising a risk model associated with a second one of the plurality of participants, providing at least one application that is downloaded to a user device of the plurality of participants, wherein the at least one application is configured to divide at least a portion of the health information into obfuscated health information, and wherein the sequence of instructions comprise code for:
performing a privacy-preserving computation over the obfuscated health information by operation of:
means for receiving, by the at least one application, a random triple from a computation manager, the random triple being based at least in part on a Beaver triple generated by the computation manager;
means for performing, by the at least one application, the privacy-preserving computation to determine at least one computation result, the privacy-preserving computation being performed over the obfuscated health information and based at least in part on the random triple; and
means for accessing, over a network, one or more external corpora to retrieve online information comprising at least one external data value that is not in the plurality of data sets, then triggering, by a computer, a data integrity check to determine an accuracy of the privacy-preserving computation based at least in part on the at least one external data value and requesting additional data when the accuracy is below a threshold.

29. The system of claim 28, wherein the plurality of participants comprises at least one of a user, a patient, a physician, an insurance applicant, an insurance provider, a genomics sequencing entity, a genomics company, or a pharmaceutical company, and wherein the first data set comprises at least one of a genome sequence or a set of questionnaire responses, and wherein the second data set describes a risk model.

30. The system of claim 28, further comprising instructions which, when stored in memory and executed by the processor cause the processor to perform further acts of:
determining at least one integrity value based at least in part on the data integrity check.

* * * * *